US012740756B2

(12) United States Patent
Von Ramm et al.

(10) Patent No.: US 12,740,756 B2
(45) Date of Patent: Sep. 22, 2026

(54) SYSTEMS, METHODS AND ELECTRODES FOR 4-DIMENSIONAL ULTRASOUND PULSE-ECHO IMAGING OF THE NECK AND UPPER AIRWAY

(71) Applicant: Volumetrics Medical Systems, LLC, Durham, NC (US)

(72) Inventors: Olaf Von Ramm, Efland, NC (US); Kent Moore, Charlotte, NC (US)

(73) Assignee: Volumetrics Medical Systems, LLC, Durham, NC (US)

(*) Notice: Subject to any disclaimer, the term of this patent is extended or adjusted under 35 U.S.C. 154(b) by 35 days.

(21) Appl. No.: 18/757,654

(22) Filed: Jun. 28, 2024

(65) Prior Publication Data

US 2024/0350112 A1 Oct. 24, 2024

Related U.S. Application Data

(60) Continuation of application No. 17/411,128, filed on Aug. 25, 2021, now Pat. No. 12,027,157, which is a (Continued)

(51) Int. Cl.
*A61B 8/08* (2006.01)
*A61B 5/00* (2006.01)
(Continued)

(52) U.S. Cl.
CPC .............. *A61B 8/08* (2013.01); *A61B 5/0295* (2013.01); *A61B 5/0826* (2013.01); *A61B 5/087* (2013.01);
(Continued)

(58) Field of Classification Search
CPC ... A61B 5/0295; A61B 5/0806; A61B 5/0826; A61B 5/087; A61B 5/1116; A61B 5/369;
(Continued)

(56) References Cited

U.S. PATENT DOCUMENTS 1,129,588 A 2/1915 Onderdong
5,795,297 A 8/1998 Daigle
(Continued)

OTHER PUBLICATIONS

Al-Bed et al., "Detection of Airway Occlusion in Simulated Obstructive Sleep Apnea/Hypopnea using Ultrasound: an Invitro Study," 32nd Annual International Conference of the IEEE EMBS, Buenos Aires, Argentina, Aug. 31-Sep. 4, 2010.
(Continued)

*Primary Examiner* — Mark D Remaly
(74) *Attorney, Agent, or Firm* — Stanek Lemon Crouse & Meeks, PA

(57) ABSTRACT

A system for imaging an airway for assessing obstructive sleep apnea (OSA) can include first and second ultrasound transducer arrays on first and second body members, respectively, configured to adhere the first and second ultrasound transducer arrays at first and second fixed positions on a neck while ultrasound scanning. A processor circuit can be coupled to the first and second ultrasound transducer arrays, the processor circuit configured to operate the first and second ultrasound transducer arrays for pulse-echo imaging of a soft tissue-airway interface to generate respective first and second volumetric ultrasound image data sets in real-time to provide an integrated volumetric image of the soft tissue-airway interface from the first and second fixed positions on the neck.

11 Claims, 14 Drawing Sheets

Related U.S. Application Data division of application No. 15/233,540, filed on Aug. 10, 2016, now Pat. No. 11,129,586.

(60) Provisional application No. 62/328,401, filed on Apr. 27, 2016, provisional application No. 62/255,715, filed on Nov. 16, 2015, provisional application No. 62/205,369, filed on Aug. 14, 2015.

(51) Int. Cl.

| | |
|---|---|
| ***A61B 5/0295*** | (2006.01) |
| ***A61B 5/08*** | (2006.01) |
| ***A61B 5/087*** | (2006.01) |
| ***A61B 6/03*** | (2006.01) |
| ***A61B 8/00*** | (2006.01) |
| ***A61B 8/02*** | (2006.01) |
| ***G06F 3/16*** | (2006.01) |
| ***G10L 15/18*** | (2013.01) |
| ***G10L 15/22*** | (2006.01) |
| *G10L 15/183* | (2013.01) |
| *G10L 15/26* | (2006.01) |

(52) U.S. Cl.

CPC ............ *A61B 5/4812* (2013.01); *A61B 6/032* (2013.01); *A61B 8/02* (2013.01); *A61B 8/4245* (2013.01); *A61B 8/4483* (2013.01); *A61B 8/483* (2013.01); *G06F 3/16* (2013.01); *G10L 15/1815* (2013.01); *G10L 15/22* (2013.01); *G10L 15/183* (2013.01); *G10L 2015/221* (2013.01); *G10L 2015/225* (2013.01); *G10L 15/26* (2013.01)

(58) Field of Classification Search

CPC ....... A61B 5/389; A61B 5/398; A61B 5/4812; A61B 5/4818; A61B 6/032; A61B 8/02; A61B 8/08; A61B 8/4227; A61B 8/4236; A61B 8/4245; A61B 8/44; A61B 8/4455; A61B 8/4483; A61B 8/4494; A61B 8/466; A61B 8/483; G06F 3/16; G10L 15/1815; G10L 15/183; G10L 15/22; G10L 15/26; G10L 2015/221; G10L 2015/225

See application file for complete search history.

(56) References Cited

U.S. PATENT DOCUMENTS

| | | | |
|---|---|---|---|
| 6,159,153 | A | 12/2000 | Dubberstein et al. |
| 7,697,568 | B1 | 4/2010 | Zhang et al. |
| 2004/0167126 | A1 | 8/2004 | Craig et al. |
| 2006/0056651 | A1 | 3/2006 | Yao |
| 2007/0255137 | A1 | 11/2007 | Sui et al. |
| 2008/0281197 | A1 | 11/2008 | Wiley et al. |
| 2009/0259128 | A1 | 10/2009 | Stribling |
| 2010/0191119 | A1 | 7/2010 | Muthya et al. |
| 2010/0246760 | A1 | 9/2010 | Li et al. |
| 2011/0079082 | A1 | 4/2011 | Yoo et al. |
| 2011/0190629 | A1 | 8/2011 | Guenther et al. |
| 2011/0295119 | A1 | 12/2011 | Miller et al. |
| 2012/0083717 | A1 | 4/2012 | Alleman et al. |
| 2013/0046181 | A1 | 2/2013 | Al-Abed et al. |
| 2013/0289401 | A1 | 10/2013 | Colbaugh et al. |
| 2014/0277252 | A1 | 9/2014 | Hyde et al. |
| 2014/0321726 | A1 | 10/2014 | Shin et al. |
| 2014/0340994 | A1 | 11/2014 | Calvarese |
| 2014/0343429 | A1 | 11/2014 | Jensen et al. |
| 2015/0290001 | A1 | 10/2015 | Douglas |

OTHER PUBLICATIONS

Al-Bed et al., "In Vivo Characterization Of Ultrasonic Transducers for the Detection of Airway Occlusion in Sleep Disordered Breathing," 33rd Annual International Conference of the IEEE EMBS, Boston, MA, Aug. 30-Sep. 3, 2011, pp. 7687-7690.

Al-Abed et al., "Upper Airway Occlusion Detection Using a Novel Ultrasound Technique," 34th Annual International Conference of the IEEE EMBS, San Diego, CA, Aug. 28-Sep. 1, 2012, pp. 5650-5653.

Chou et al., "Tracheal rapid ultrasound exam (T.R.U.E.) for confirming endotracheal tube placement during emergency intubation," Resuscitation, vol. 82, 2011, pp. 1279-1284.

Chou et al., "Real-time tracheal ultrasonography for confirmation of endotracheal tube placement during cardiopulmonary resuscitation," Resuscitation, vol. 84, 2013, pp. 1708-1712.

Dausch et al., "In Vivo Real-Time 3-D Intracardiac Echo Using PMUT Arrays," IEEE Transactions on Ultrasonics, Ferroelectrics, and Frequency Control, vol. 61, No. 10, Oct. 2014, pp. 1754-1764.

Khuri-Yakub et al., "Capacitive micromachined ultrasonic transducers for medical imaging and therapy," J Micromech Microeng. Vol. 21, No. 5, May 2011, pp. 054004-054014.

Kristensen, M.S., "Ultrasonography in the management of the airway," Acta Anaesthesiol Scand, 2011, vol. 55, pp. 1155-1173.

Kwok et al., "Development of the Bi-Directional Ultrasound System for Base of Tongue Imaging," Comput. Biol. Med., 1994 vol. 24, No. 4, pp. 295-304.

Lahav et al., "Tongue Base Ultrasound: A Diagnostic Tool for Predicting Obstructive Sleep Apnea," The Annals of Otology, Rhinology and Laryngology, Mar. 2009, vol. 118, No. 3, pp. 179-184.

Liu et al. "Sonographic Measurement of Lateral Parapharyngeal Wall Thickness in Patients with Obstructive Sleep Apnea," Sleep, Vo. 30, No. 11, 2007, pp. 1503-1508.

Moore et al., "A Practical Method for Describing Patterns of Tongue-Base Narowing (Modification of Fujita) in Awake Adult Patients with Obstructive Sleep Apnea," J Oral Maxillofac Surg, vol. 60, 2002, pp. 252-260.

Muslu et al., "Use of Sonography for Rapid Identification of Esophageal and Tracheal Intubations in Adult Patients," J Ultrasound Med, 2011, vol. 30, pp. 671-676.

Or et al., "Multiplanar 3D ultrasound imaging to assess the anatomy of the upper airway and measure the subglottic and tracheal diameters in adults," Br J Radiol, 2013, 13 pages.

Qiu et al., "Piezoelectric Micromachined Ultrasound Transducer (PMUT) Arrays for Integrated Sensing, Actuation and Imaging," Sensors, vol. 15, 2015, pp. 8020-8041.

Shafiee et al., "A Multi-Feature Classification Approach to Detect Sleep Apnea in an Ultrasonic Upper Airway Occlusion Detector System," 2014 IEEE, pp. 254-257.

Singh et al., "Use of Sonography for Airway Assessment," J Ultrasound Med, 2010, vol. 29, pp. 79-85.

Stuntz et al., "The effect of sonologist experience on the ability to determine endotracheal tube location using transtracheal ultrasound," American Journal of Emergency Medicine, vol. 32, 2014, pp. 267-269.

Uya et al. "Can Novice Sonographers Accurately Locate an Endotracheal Tube With a Saline-filled Cuff in a Cadaver Model? A Pilot Study," Society for Academic Emergency Medicine, 2012, pp. 361-364.

Werner et al. "Pilot Study to Evaluate the Accuracy of Ultrasound in Confirming Endotracheal Tube Placement," Annals of Emergency Medicine, vol. 46, No. 3, Sep. 2005, Research Forum Abstracts, p. S4.

Wojtczak, Jacek A., "Submandibular Sonography: Assessment of Hyomental Distances and Ratio, Tongue Size, and Floor of the Mouth Musculature Using Portable Sonography," J Ultrasound Med, 2012, vol. 31, pp. 523-528.

Yang et al., "A flexible piezoelectric micromachined ultrasound transducer," RSC Adv., vol. 3, 2013, p. 24900-24905.

Bashford et al., "Speckle structure in three dimensions," J. Acoust. Soc. Am, 98 (1), Jul. 1995, pp. 35-42.

Miss et al., "Real time ultrasound guided endotracheal intubation should strive for identification of esophageal intubation," Resuscitation, 85, 2013, 1 page.

(56) References Cited

OTHER PUBLICATIONS

Schmidt, et al., "Real-Time Three-Dimensional Echocardiography for Measurement of Left Ventricular Volumes," The American Journal of Cardiology, 84 (12), Dec. 1999, pp. 1434-1439.
Shiota, et al., "Real-time Three-dimensional Echocardiography for Determining Right Ventricular Stroke Volume in an Animal Model of Chronic Right Ventricular Volume Vverload," Circulation, 97(19), May 1998, pp. 1897-1900.
Smith et al., "High-Speed Ultrasound Volumetric Imaging System Part I: Transducer Design and Beam Steering," IEEE Transactions on Ultrasonics, Ferroelectrics and Frequency Control, 38 (2), Mar. 1991, pp. 100-108.
Trahey et al., "A Quantitative Approach to Speckle Reduction Via Frequency Compounding," Ultrasonic Imaging, 8 (3), Jul. 1986, pp. 151-164.
Trahey et al., "Speckle Pattern Correlation with Lateral Aperture Translation: Experimental Results and Implications for Spatial Compounding," IEEE Transactions on Ultrasonics, Ferroelectrics and Frequency Control, UFFC-33 (3), May 1986, pp. 257-264.
Von Ramm et al., "High-Speed Ultrasound Volumetric Imaging System Part II: Parallel Processing and Image Display," IEEE Transactions on Ultrasonics, Ferroelectrics and Frequency Control, 38 (2), Mar. 1991, pp. 109-115.
Smith, et al., "Measurements and Analysis of Speckle in Ultrasound B-Scans," Acoustical Imaging, vol. 10, edited by Pierre Alais and Alexander F. Metherell, The Journal of the Acoustical Society of America 73, 1404 (1983), pp. 195-211.

SYSTEMS, METHODS AND ELECTRODES FOR 4-DIMENSIONAL ULTRASOUND PULSE-ECHO IMAGING OF THE NECK AND UPPER AIRWAY

CROSS-REFERENCE TO RELATED APPLICATIONS

This application is a continuation of and claims priority to U.S. patent application Ser. No. 17/411,128, entitled "Systems, Methods and Electrodes for 4-Dimensional Ultrasound Pulse-Echo Imaging of the Neck and Upper Airway," filed Aug. 25, 2021, which is divisional of and claims priority to U.S. patent application Ser. No. 15/233,540, entitled "Devices, Methods, Systems, and Computer Program Products for 4-Dimensional Ultrasound Imaging," filed Aug. 10, 2016, which claims the benefit of U.S. Provisional Patent Application No. 62/205,369 entitled "Apparatus and Method for 4-Dimensional Imaging of A Patient's Airway," filed Aug. 14, 2015, U.S. Provisional Patent Application No. 62/255,715 entitled "Apparatus and Method for 4-Dimensional Imaging of a Patient's Airway," filed Nov. 16, 2015, and U.S. Provisional Patent Application No. 62/328,401 entitled "Apparatus and Method for 4 Dimensional Imaging of a Patient's Airway," filed Apr. 27, 2016, each of which is hereby incorporated by reference in its entirety.

BACKGROUND

The present disclosure relates to medical devices and methods for observing and gathering 4D real-time ultrasound data.

Obstructive sleep apnea (OSA) is a difficult yet indolent condition to both diagnose and treat. While both in-lab polysomnogram and home-based portable sleep studies have become more or less commonplace in providing a diagnosis of OSA, many patients diagnosed with OSA are unable for multiple reasons to utilize Continuous Positive Airway Pressure (CPAP), the most commonly prescribed nonsurgical therapy for OSA. At the same time, however, the ability of the clinician to predict response to alternative nonsurgical and surgical therapies in any given individual has been problematic.

SUMMARY

A system for imaging an airway for assessing obstructive sleep apnea (OSA) can include first and second ultrasound transducer arrays on first and second body members, respectively, configured to adhere the first and second ultrasound transducer arrays at first and second fixed positions on a neck while ultrasound scanning. A processor circuit can be coupled to the first and second ultrasound transducer arrays, the processor circuit configured to operate the first and second ultrasound transducer arrays for pulse-echo imaging of a soft tissue-airway interface to generate respective first and second volumetric ultrasound image data sets in real-time to provide an integrated volumetric image of the soft tissue-airway interface from the first and second fixed positions on the neck.

BRIEF DESCRIPTION OF THE DRAWING(S)

DETAILED DESCRIPTION

Figure 1:
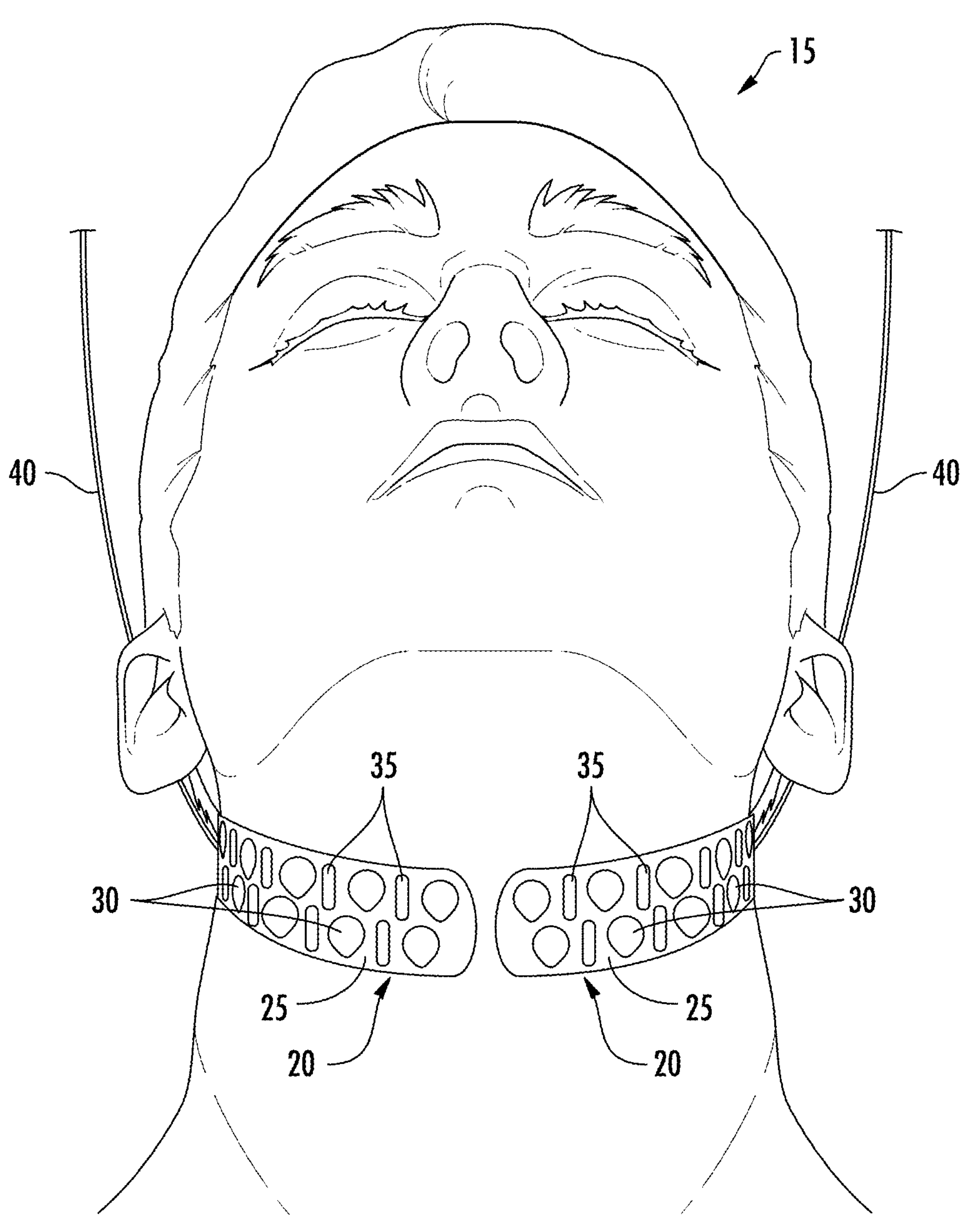
FIG. 1 is a perspective view from above of a patient's head and neck with ultrasound transducer array strips applied to the patient's neck for imaging the patient's upper airway in some embodiments according to the invention.

The present invention now will be described more fully hereinafter with reference to the accompanying drawings in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Nocturnal upper airway soft tissue obstruction, which is the basic mechanism of OSA, results from soft tissue collapse of the upper airway and occurs during various stages of sleep, most commonly during supine rapid eye movement (REM) sleep. Conventionally, electroencephalogram (EEG) monitoring is often required to detect the specific stage of sleep during which the soft tissue collapse is occurring in order to discern the most vulnerable period for airway obstruction.

Expansion of the nocturnal upper airway (as opposed to by-passing) is the basic and most common conventional method used for treatment of OSA. Such expansion can be achieved using a wide variety of current nonsurgical (e.g., CPAP, weight loss, oral appliance) and surgical therapies. For example, CPAP induces diffuse (e.g., vertical anatomic) airway expansion via pressurization of the upper airway. Oral appliances and directed surgical therapies produce their effect by both direct and indirect (yet more focused) mechanical airway expansion.

Of some interest (particularly in situations in which patients are unable to use CPAP) is the need to identify the specific sites of nocturnal upper airway narrowing using both noninvasive and non-damaging imaging modalities during various stages of sleep. Supine REM sleep refers to the body position and stage of sleep that are most commonly recognized as the most vulnerable position and stage of sleep associated with OSA in predisposed individuals. As opposed to diffuse expansion produced by CPAP, the site of upper airway narrowing, if correctly identified anatomically, can be used as the location and target for more focused airway expansion therapies. More recently, titration studies have been developed to allow physicians to more accurately prescribe oral appliance therapies that are likely to be effective and/or identify a target protrusive position that will provide the best response to oral appliance therapy. An example is the MATRx system from Zephyr Sleep Technologies, which allows titration of the patient's mandibular position as an indirect method of inducing airway expansion during natural sleep.

As another example, evaluation of the nocturnal supine upper airway using cine magnetic resonance imaging (MRI) is exceedingly difficult, as creating the ability for any subject to undergo natural (e.g., non-drug induced) sleep in the loud and unfriendly environment of an MRI scanner is exceedingly difficult and expensive. Moreover, the ability to physically monitor the stage of sleep (using very specialized EEG electrodes) while in the magnetic field of a typical MRI unit in a real-time fashion is a significant technological challenge due to induced electromagnetic artifact, and only a small handful of research institutions have the tools and expertise to perform such an evaluation.

Similarly, computerized tomography (CT) evaluation of upper airway obstruction during supine natural sleep subjects the patient to exceedingly high dosages of radiation, and the ability to couple the CT images with the stages of sleep and phase of respiration most prone to airway obstruction is challenging. Accordingly, as appreciated by the present inventors, medical-grade CT evaluation may not be a viable or widely applicable imaging modality for assessing airway anatomy.

Another conventional diagnostic method known as drug-induced sleep endoscopy (DISE) uses subjective visual examination via traditional endoscopic techniques to evaluate upper airway obstruction. DISE has been expounded as a manner to somewhat "replicate" the patterns of soft tissue collapse using Propofol and/or Dexmetomidine-induced anesthesia and has been proposed as a method to evaluate the upper airway in subjects considering upper airway surgery. The blood concentrations needed for either of these medications to induce a somewhat "REM-like" state of sleep in any given individual is yet to be discerned, however, leading to subjective "over-dosage" or "under-dosage" for any given individual. Accordingly, the degree of airway narrowing noted during subjective endoscopic examination is subject to wide (and varied) interpretation.

Optical Coherence Tomography (OCT) is one of the newest imaging modality that has been introduced for upper airway measurements. While the most accurate (in terms of resolution), this technology suffers from practical limitations of pullback length and speed, as well as being an invasive endoscopic study requiring trans-nasal or trans-oral catheter placement. Irritation of the catheter tip producing reactive mucosal and muscular contractions and excess secretions of the upper airway may be problematic in causing artifactual ("reactive") airway narrowing, thereby confusing the interpretation of the results.

Conventional ultrasound evaluation of the upper airway, while potentially very attractive as a practical and non-damaging method to evaluate the airway, has been used previously in anesthesia-type or emergency type applications to evaluate airway and tracheal anatomy which may complicate ventilatory management under drug-induced sedative/anesthetic states. As appreciated by the present inventors, the interpretation of ultrasonic evaluation of the upper airway is difficult, however, due to the unique 3-dimensional anatomy of the upper airway, the bony confines of the mandible and the base of skull surrounding the upper airway (which act to impede ultrasonic transmission and signal reception), and the air/soft tissue interface boundaries that often serve to prevent the capture of complete soft tissue airway anatomy.

The relevant tissues visualized in the upper airway using ultrasound include the thyroid cartilage; the cricoid cartilage; the tracheal rings; and the interface of the tracheal mucosa, the glottis, the base of tongue, and the upper airway, including the pharyngeal wall, soft palate, epiglottis, and the air within the upper airway. The esophagus, thyroid gland, cervical spine, mandible, hyoid bone, and common carotid arteries represent the relevant surrounding anatomic structures. Typically, cartilage has a hypoechoic (dark) sonographic appearance. At the same time, due to the significant difference in acoustic impedance between soft tissue and air, sound waves at the air-mucosal interface (A-M interface) along the anterior border of the airway are strongly reflected, resulting in a hyperechoic (bright) sonographic appearance. In routine 2-dimensional ultrasound, the air within the airway lumen generally does not permit transmission and return of ultrasound, and the lumen and posterior wall are therefore not visualized.

It will be understood that the volumetric ultrasound image data sets described herein can be generated from a 3-dimensional volume of a body scanned by an ultrasound imaging system coupled to a plurality of ultrasound transducer arrays. The plurality of ultrasound transducer arrays can be located, for example, separate from one another relative to the patient's upper airway (e.g., on opposing sides of the airway, or positioned to image the airway from different directions, so that the different fields of imaging by the separate transducers can be combined to provide an image that shows portions of the airway that would otherwise be in a shadow). Accordingly, when the ultrasound imaging system scans the upper airway, a plurality of separate volumetric ultrasound image data sets can be generated (i.e., one volumetric ultrasound image data set per array). Those volumetric ultrasound image data sets can be combined by the ultrasound imaging system (or another processing system) to generate an integrated volumetric image that can provide a more complete 3-D rendering of the upper airway using the ultrasound data compared to imaging performed by a single ultrasound transducer or alternatively, fewer ultrasound transducers. It will be further understood that the integrated volumetric image can be presented over a time interval so as to provide a 4-D volumetric image. Ultrasound can be a non-invasive, non-traumatic, real-time, non-ionizing imaging method that can be used to evaluate OSA and other medical conditions that require monitoring such as in an ICU, during pregnancies, and other portable assessments.

It will be understood that, in some embodiments, the separate volumetric ultrasound image data sets can be generated as static images. In still other embodiments according to the invention, the separate volumetric ultrasound image data sets can be generated as real-time separate volumetric ultrasound image data sets.

As used herein, the term "real time" is defined to include time intervals that may be perceived by a user as having little or substantially no delay associated therewith. For example, when a volume rendering using an acquired ultrasound dataset is described as being performed in real time, a time interval between acquiring the ultrasound dataset and displaying the volume rendering based thereon may be in a range of less than 1 second to reduce a time lag between an adjustment and a display that shows the adjustment. For example, some systems may typically operate with time intervals of about 0.10 seconds. Time intervals of more than one second may also be used.

It will be further understood that although many of the embodiments described herein, discuss imaging of the upper airway, the present invention may be utilized to image other parts of the anatomy, such as hearts, etc. Accordingly, the ultrasound imaging system according to the present invention can be utilized to provide integrated 3-D volumetric images and 4-D integrated volumetric images of any tissue. As used herein, the term "tissue" includes biological tissue in a body.

It will be further understood that the generation of the volumetric ultrasound imaging data sets described herein can be carried out by, for example, the volumetric scanning techniques described in, for example, U.S. Pat. No. 5,546,807 to Oxaal et al. entitled "High Speed Volumetric Ultrasound Imaging System" and U.S. Pat. No. 4,596,145 to Smith et al. entitled "Acoustic Orthoscopic Imaging System", the disclosures of both of which are hereby incorporated herein by reference in their entireties. For example, the above-described systems can be utilized to provide a front end for the RF channel data, a receive processor, a detector, and a scan converter which may be incorporated into the ultrasound imaging system or may be provided in an auxiliary system.

It will be also understood that the ultrasound imaging system in some embodiments according to the invention can generate ultrasound beams that propagate into the tissue thereby generating reflections that are used for generation of the volumetric ultrasound image data sets as described in U.S. Pat. No. 5,546,807 to Oxaal et al.

It will be also understood that the functionality of the ultrasound transducers as well as the ultrasound transmitters described herein may be incorporated into an ultrasound transducer array to provide a single array that can both transmit ultrasound beams as well as process the reflections therefrom to generate the volumetric ultrasound image data sets using pulse-echo imaging as described in, for example, U.S. Pat. No. 4,694,434 to von Ramm et al. entitled "Three Dimensional Imaging System", the entire disclosure of which is incorporated herein by reference.

The volumetric ultrasound image data sets are formed by steering the ultrasound beams in the elevation direction and in the azimuth direction so that the steered ultrasound beams scan the target volume within the tissue (such as the targeted portion of the upper airway). The receive ultrasound beams are formed in the elevation direction and in the azimuth direction from the reflections of the steered ultrasound beams in the tissue. The formed receive ultrasound beams represent the echoes of the steered ultrasound beams from the tissue. Because the receive ultrasound beams are formed in the azimuth and elevation directions, the volumetric ultrasound image data set corresponding thereto, represent echoes of the steered ultrasound beams in the 3-dimensions. In some embodiments according to the invention, the receive ultrasound beams can be formed using receive mode parallel processing and the generation of the 3D ultrasound imaging data sets can be performed as described, for example, in U.S. Pat. No. 4,694,434 to von Ramm et al. entitled "Three Dimensional Imaging System", the entire disclosure of which is incorporated herein by reference.

Turning now to FIGS. 1-3B, embodiments of a medical device for generating 4-dimensional nocturnal airway quantitative data in a patient are shown in which a series of small and lightweight ultrasound transducers and transmitters are placed in partially around the retromandibular and submandibular regions of the patient's neck to allow noninvasive and non-damaging quantitative assessment (in a real-time fashion) of nocturnal upper airway anatomic narrowing.

Figure 2:
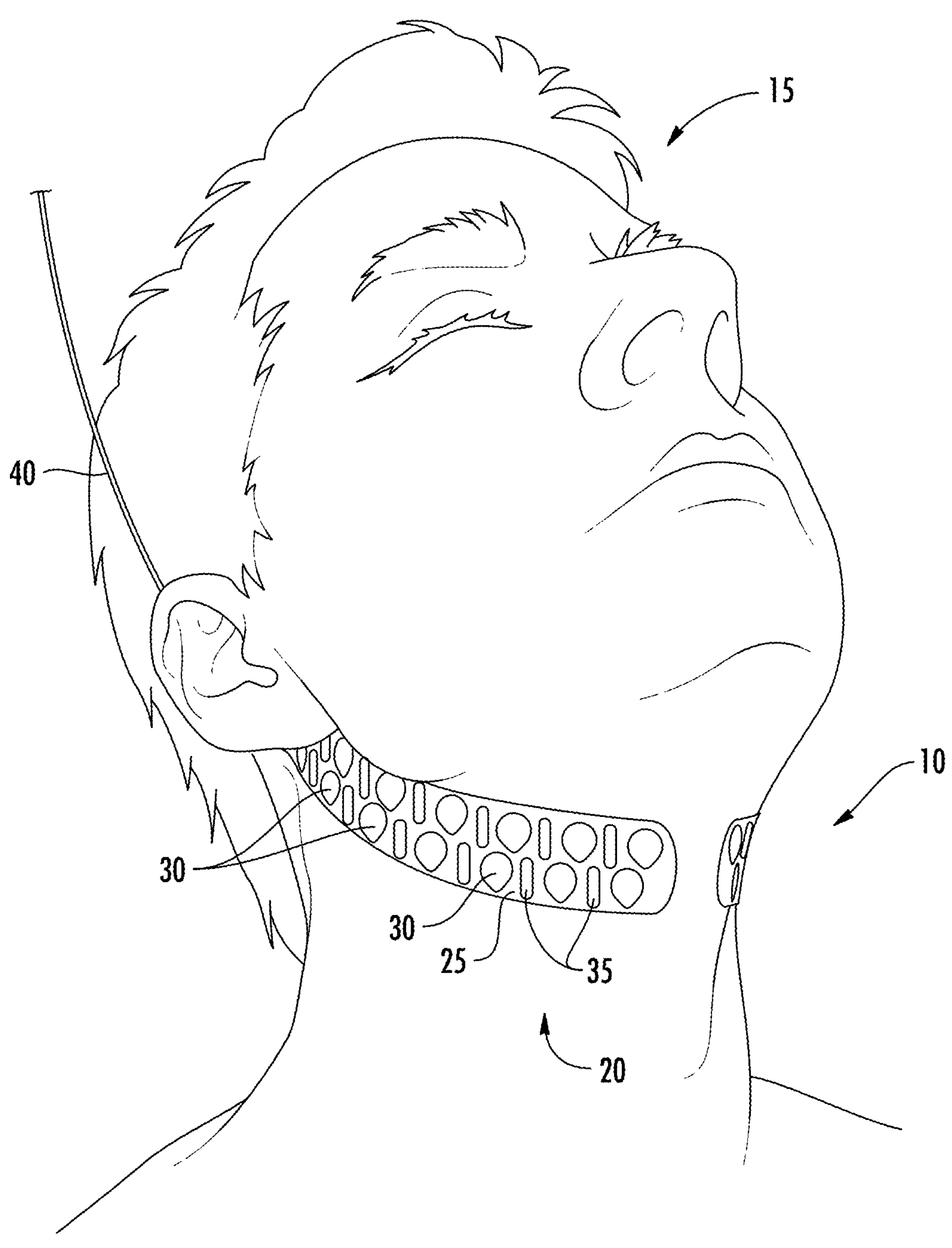
FIG. 2 is a perspective view from the side of the patient's head and neck with the ultrasound transducer array strips of FIG. 1 applied to the neck for imaging the patient's upper airway in some embodiments according to the invention.
Figure 3A:
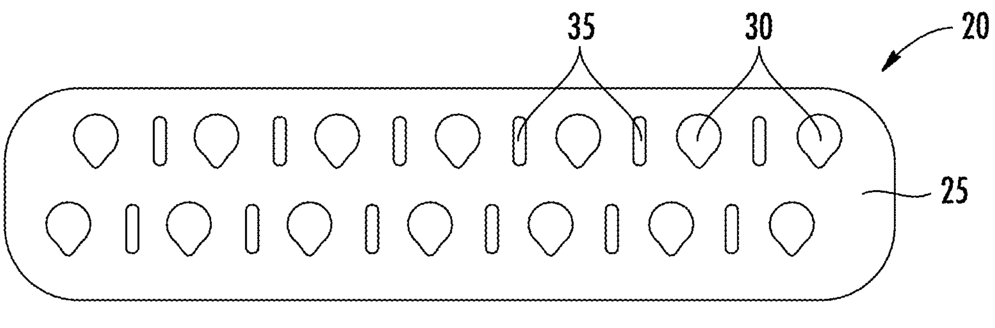
FIG. 3A is a front plan view of one of the electrode strips of FIGS. 1 and 2 in some embodiments according to the invention.
Figure 3B:
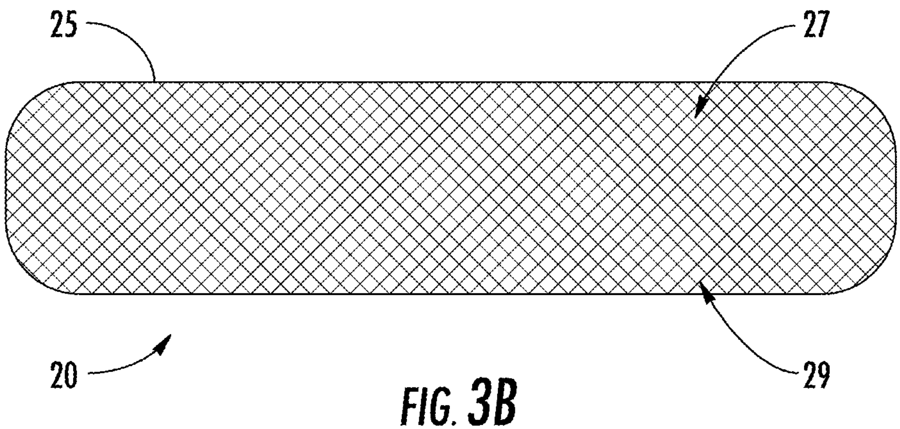
FIG. 3B is a rear plan view of the electrode strip of FIG. 3A in some embodiments according to the invention.

With reference to FIGS. 1-3B, for example, a device 10 is illustrated for imaging a patient's airway for assessing obstructive sleep apnea (OSA) in the patient 15, where the device includes at least one electrode strip (i.e., ultrasound transducer array strip) 20. In the some embodiments, two electrode strips 20 are provided for positioning separately on the patient's neck, just below the patient's mandible. Each electrode strip 20 includes a body member 25 that defines an engaging surface 29 (shown in FIG. 3B) that includes an adhesive 27, such as a pressure sensitive adhesive. The body member 25 is configured to be secured to a retromandibular and submandibular region of the patient's neck via the adhesive, as shown in FIGS. 1 and 2.

An array of ultrasound transducers 30 may be provided that are supported by the body member 25. For example, in some embodiments, the body member 25 may be made of a silicone rubber material, and a sparse array of ultrasound transducers 30 may be embedded in or otherwise attached to the silicone rubber material (e.g., attached to an inner or outer surface of the body member, such as via an adhesive, coating, film, or mechanical fastening means). In some embodiments, for example, the ultrasound transducers 30 may comprise a piezoelectric material, such as PZT (lead zirconate titanate) crystals, bound to brass backings or discs or PMN-PT (lead magnesium niobate-lead titanate). In some embodiments, for example, the ultrasound transducers 30 may comprise a piezoelectric material, such as PVDF (polyvinylidene fluoride or polyvinylidene difluoride). As another example, in other embodiments, the body member 25 may comprise multiple layers of a substrate, such as layers of polymer film or paper-based layers. In such embodiments, the array of ultrasound transducers 30 may be adhered or otherwise attached to the body member 25 between two of the substrate layers or may be attached to an inner or outer surface of the body member 25, through adhesive or mechanical fastening methods. In some embodiments, each of the ultrasound transducers 30 represents a separate array of ultrasound transducers.

Each ultrasound transducer 30 of the array may be configured to receive ultrasound waves and to convert the ultrasound waves into electric impulses. Examples of ultrasound transducers that may be use include OmniScan® iX UT transducers from Olympus NDT (Quebec, Canada), Data Acquisition (DAQ) system transducers from National Instruments (Austin, TX), or the like. The at least one electrode strip 20 may be configured to be disposed on one side of the patient's neck, and the respective array of ultrasound transducers 30 may be configured to receive ultrasound waves transmitted by a corresponding array of ultrasound transmitters positioned on an opposite side of the patient's neck. In some cases, the at least one electrode strip 20 may further comprise an array of ultrasound transmitters 35, as shown in the figures.

For example, in some cases, as illustrated, two electrode strips 20 may be provided, with the electrode strips being positioned on opposite sides of the patient's neck. A first electrode strip (e.g., leftmost electrode strip 20 in FIG. 1) may include an array of ultrasound transducers 30 and an array of ultrasound transmitters 35, and a second electrode strip (e.g., rightmost electrode strip 20 in FIG. 1) may also include an array of ultrasound transducers 30 and an array of ultrasound transmitters 35. Because they are positioned on opposite sides of the patient's neck in the embodiment of FIG. 1, the array of ultrasound transducers 30 of the first electrode strip 20 (e.g., leftmost) may be configured to receive the ultrasound waves transmitted by the array of ultrasound transmitters 35 of the second electrode strip 20 (rightmost), and the array of ultrasound transducers 30 of the second electrode strip 20 (rightmost) may be configured to receive the ultrasound waves transmitted by the array of ultrasound transmitters 35 of the first electrode strip 20 (leftmost).

In other embodiments, however, a first electrode strip may be provided that comprises the array of ultrasound transducers 30, and a second electrode strip may be provided that comprises the array of ultrasound transmitters 35. In this way, with the first electrode strip 20 in position on one side of the patient's neck and the second electrode strip positioned on the other side of the patient's neck, the array of ultrasound transducers of the first electrode strip may be configured to receive the ultrasound waves transmitted by the array of ultrasound transmitters of the second electrode strip. Thus, in this example, the transmission of ultrasound signals may only occur in one direction, rather than bi-directionally as in the depicted embodiments.

The configuration of the electrode strips 20 may vary according to the size of the patient and the size of his or her neck, the patient's particular anatomy, and/or the medical professional's preferences. In some cases, for example, the body member 25 may have a rectangular shape and may be approximately 4 mm wide by 10 mm long. Moreover, there may be different numbers and arrangements of the ultrasound transducers and transmitters included on each strip 20. For example, in one case, an electrode strip that includes the array of ultrasound transducers (and no ultrasound transmitters) may have about 10-14 (e.g., 12) ultrasound transducers 30 arranged on the 4×10 mm body member 25. A second electrode strip having the ultrasound transmitters 35 (and no ultrasound transducers) may be configured such that there are about 6-10 (e.g., 7) ultrasound transmitters 35 arranged on the 4×10 mm body member 25. The thickness of the transducer in one example may be about 0.58 mm, and a brass layer may be used as a backing layer. The ultrasound transducers 30 may be configured to match the frequency of the ultrasound transmitters 35, and in some cases the frequency may be around 3 MHZ.

Figure 5:
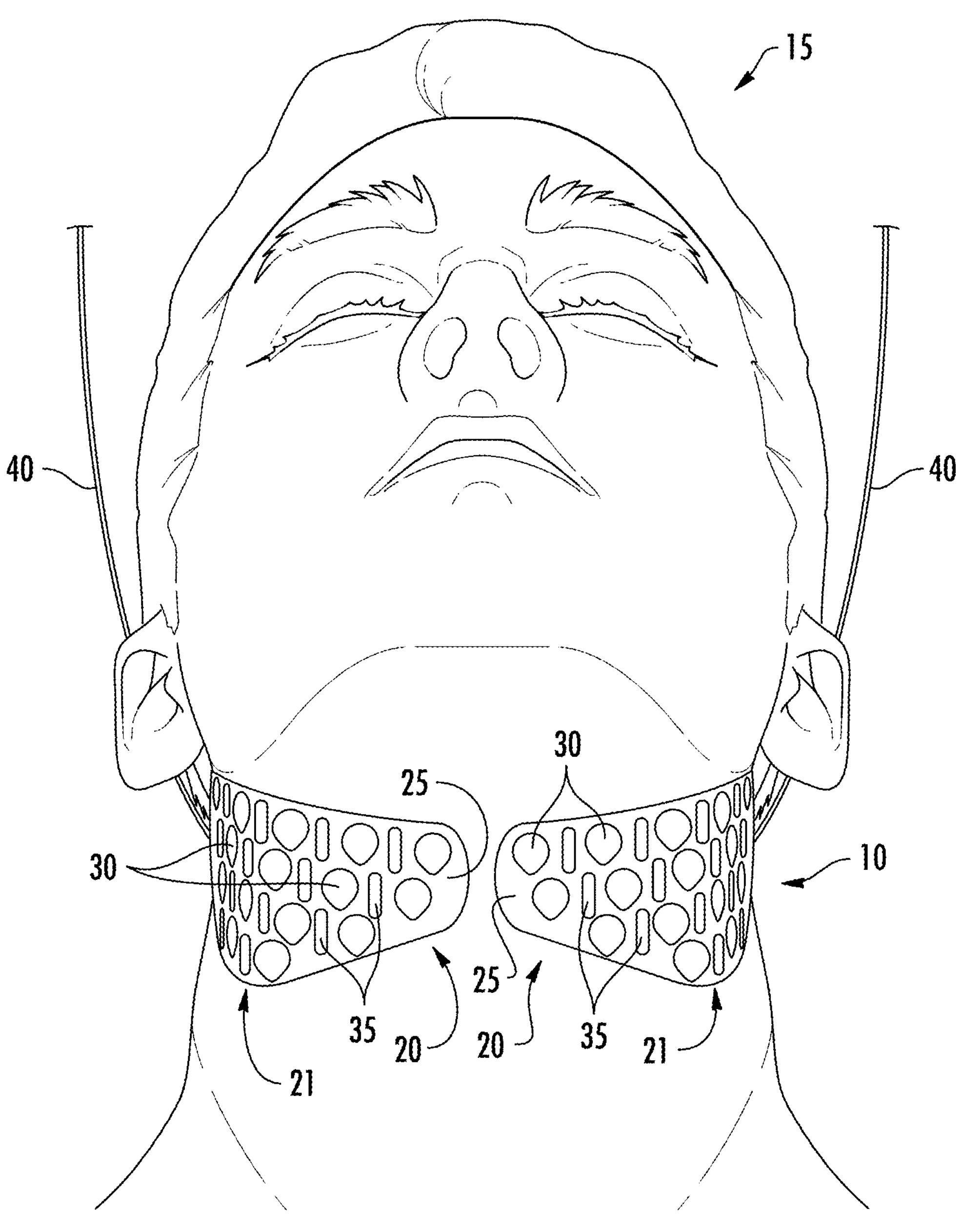
FIG. 5 is a perspective view from above of a patient's head and neck with ultrasound transducer array strips applied to the patient's neck for imaging the patient's upper airway in some embodiments according to the invention.
Figure 6:
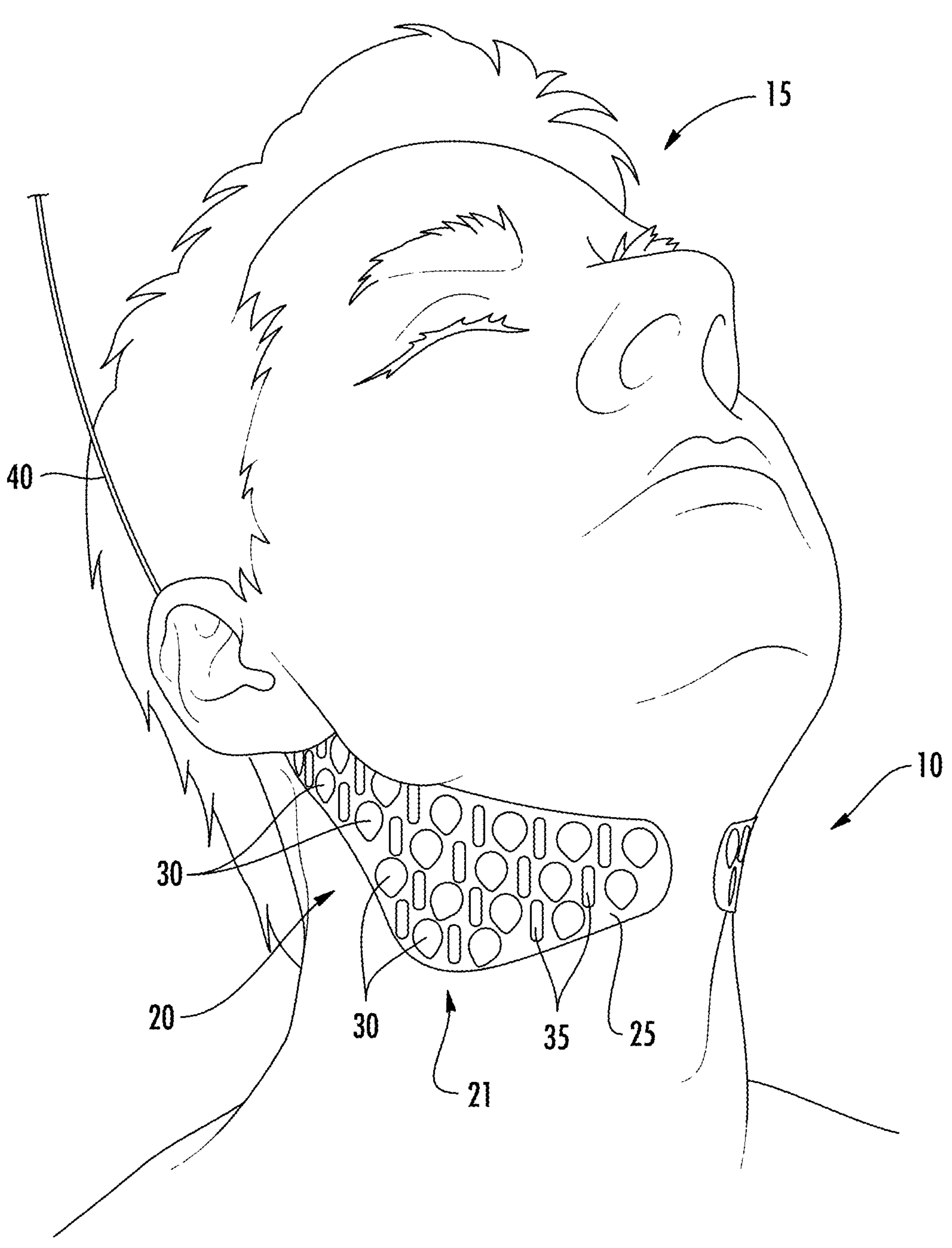
FIG. 6 is a perspective view from the side of a patient's head and neck with the ultrasound transducer array strips of FIG. 5 applied to the patient's neck for imaging the patient's upper airway in some embodiments according to the invention.

In other embodiments, however, examples of which are shown in FIGS. 5 and 6, one or more of the electrode strips 20 may extend inferiorly from the retromandibular region, so as to permit more inferior airway assessment. For example, as illustrated in FIGS. 5 and 6, each electrode strip 20 may include an extended portion 21 extending inferiorly from the retromandibular region which may include additional ultrasound transducers 30 and/or ultrasound transmitters 35. In the depicted example, two additional rows of ultrasound transducers 30 and ultrasound transmitters 35 are included in the extended portion 21, the additional rows being shorter than the other rows to allow them to fit in the extended portion.

In some the embodiments, each of the two electrode strips 20 has both ultrasound transducers 30 and ultrasound transmitters 35, each electrode strip may have between 6 and 30 ultrasound transducers and between 6 and 30 ultrasound transmitters. For example, in the depicted embodiment of FIGS. 1 and 2, each electrode strip 20 has 14 ultrasound transducers 30 and 12 ultrasound transmitters 35. In the embodiment of FIGS. 5 and 6, each electrode strip 20 has 20 ultrasound transducers 30 and 17 ultrasound transmitters 35. The ultrasound transducers 30 and the ultrasound transmitters 35 may, in some cases, be interspersed with each other (e.g., arranged in alternating fashion) across the electrode strip 20, as shown for example in FIG. 3A.

The medical devices 10 described herein may have electrode strips 20 that are, in some cases, connected via a wire lead 40 to a processor, such that the wire lead is configured to relay the electric impulses generated by the ultrasound transducers 30 to the processor for imaging the patient's airway, for combining with data received via other instrumentation that is taking other measurements while the patient is sleeping, and/or for performing calculations using one or more pieces of such data. In other embodiments, however, the device 10 may be configured such that the electric impulses corresponding to the ultrasound waves received by the various ultrasound transducers 30 are wirelessly relayed from the electrode strips 20 to the processor for further processing and analysis.

As such, ultrasound transducers may function based on different methods/principles, including the piezoelectric effect, magnetostriction, the photoacoustic effect, and/or change in capacitance. In some embodiments, the transducers 30 of the device 10 are piezoelectric ultrasonic transducers. In this regard, in some embodiments, the piezoelectric transducers may be bulk piezoelectric transducers that use the thickness-mode motion of a piezoelectric material such as, PZT (lead zirconate titanate) crystals, or single-crystal PMN-PT (lead magnesium niobate-lead titanate). In other embodiments, the piezoelectric transducers may be piezoelectric micromachined ultrasonic transducers (PMUTs). The PMUTs may be fabricated using MEMS (microelectromechanical systems) technology. Typically, PMUTs are based on the flexural motion of a thin membrane coupled with a thin piezoelectric material film (such as a film with a predetermined thickness), such as PVDF (polyvinylidene fluoride or polyvinylidene difluoride). In some embodiments, PMUTs may be diaphragm-like thin film flexural transducers formed on silicon substrates. In some embodiments, the PMUTs may comprise AIN (aluminum nitride), or ZnO (Zinc Oxide), or PZT thin films deposited/coated on a silicon substrate. In some embodiments, PMUTs may comprise enhanced flexibility in comparison with conventional rigid ultrasound transducers and/or bulk piezoelectric transducers. In some embodiments, PMUTs may comprise increased bandwidth, increased acoustic impedance match with water, and reduced voltage requirements in comparison with bulk piezoelectric transducers. In some instances, PMUTs may have the potential for integration with supporting electronic circuits, for miniaturized devices and miniaturized high frequency applications.

In some embodiments, the device 10 may constructed using CMUT (Capacitive Micromachined Ultrasonic Transducers) and MEMS (microelectromechanical systems) technology. Unlike ultrasound transducers that rely on piezoelectricity, CMUTs are transducers 30 that use a change in capacitance to create energy transduction. Because CMUTs are micromachined, it may be easier to construct 2-dimensional and 3-dimensional arrays of transducers using this technology, and a larger number of CMUTs may be able to be included in a transducer array of the electrode strips 20 described above to provide larger bandwidth as compared to other transducer technologies. In addition, it may be easier to achieve a higher operating frequency using CMUTs, due to the smaller dimensions of the ultrasound transducers.

CMUTs are generally constructed via MEMS by forming a cavity in a silicon substrate and suspending a thin layer on the top of the cavity that serves as a membrane on which a metallized layer acts an electrode together with the silicon substrate, which serves as a bottom electrode. Because CMUTs are built using silicon, integration of electronics may be included in the chip package, which may result in decreasing the fabrication complexity and lowering the costs of fabrication.

In some cases, the front-end electronics may be integrated with the CMUT array (e.g., using monolithic integration) in order to fabricate both the driving and readout electronics together with the CMUT structure, on the same substrate wafer. This may lead to improved CMUT performance as compared to other integration schemes. Thus, there may be a better signal-to-noise ratio when using CMUT ultrasound transducers as compared to piezoelectric transducers due to a reduced interconnect parasitic resistance and capacitance, a smaller die size and package, and lower power consumption. Such a monolithic approach may be especially suited for applications like CMUTs, where performance and miniaturization are of key importance, and where hundreds of thousands or even millions of interconnections may be needed between the CMUT array and the electric circuitry of the device and peripheral devices (e.g., integrated circuits, such as CMOS (Complementary Metal-Oxide-Semiconductor) chips). It will be further understood that PMUT arrays may be used in with or as an alternative to the CMUT arrays is the arrangements described above. Still further, any of the transducer devices described herein can be used in any embodiment according to the invention either singularly or in combination with any of the other transducer devices.

Regardless of how the impulses are transmitted (via for instance piezoelectricity, PMUTs, CMUTs, via wires or wirelessly), the device 10 may be configured such that the electrode strips 20 are relatively soft and malleable to provide patient comfort and to conform to the natural external neck anatomy an retromandibular regions of the patient. Customized leads may, in some cases, be fabricated following external morphological/anatomical 3-dimensional surface anatomy scans, which may in turn facilitate and provide for a more correct fit to the patient and allow for more accurate data capture. It will be understood that the term "ultrasound transducer" or "transducer" is used herein to refer to any of the technologies described herein, such as piezoelectric, PMUT, and/or CMUT trasnducers.

Moreover, embodiments of the device 10 described above may be configured to be used in conjunction with other instruments configured to collect other data relating to the patient's anatomy and sleep patterns, including one or more of an EEG, EMG chest plethysmograph, airflow sensor and/or thermistor, $SaO_2$ monitor (e.g., measuring blood-oxygen saturation levels), microphone, and actigraph. A system diagram illustrating the various instruments and their interaction with the system 50 according to one example is provided in FIG. 4. It will be understood that the system 50 can be provided by the 4D real time ultrasound imaging system shown in FIG. 8.

Figure 4:
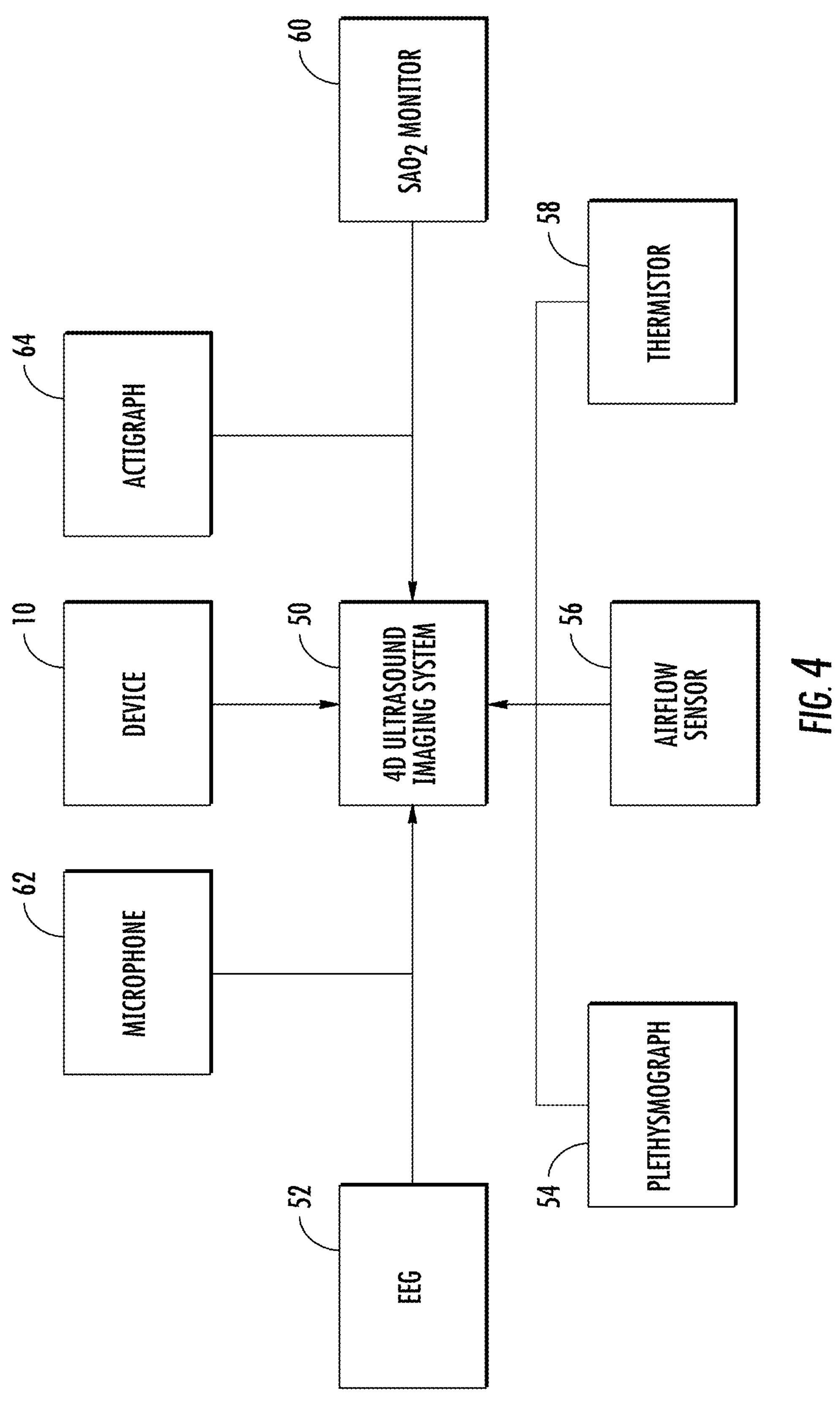
FIG. 4 is a schematic illustration of a system for collecting and processing data acquired from the ultrasound transducer arrays of embodiments disclosed herein and other instrumentation in some embodiments according to the invention.

For example, with reference to FIG. 4, once the device 10 is placed and secured to the patient's neck in the appropriate position (shown in FIGS. 1 and 2), the ultrasound transmitters 35 may be activated (e.g., via user inputs received at the system 50) to emit ultrasonic waves that reflect off the various soft tissue and air interfaces of the patient's neck. The ultrasound waves may be received at the ultrasound transducers 30 and may be converted into electric impulses by the transducers. Those impulses, in turn, may be relayed to a processor 50 that is configured to receive signals from the ultrasound transducers 30 of the device 10, as well as various other instruments that the patient may be connected to. For example, the patient may be wearing a skull cap housing an EEG 52 or separate EEG electrodes (for detecting sleep stage) and electromyography (EMG) electrodes (for detecting Rapid Eye Movement), and/or the patient may be connected to a chest plethysmograph 54. The patient may also, in some cases, have a nasal cannula installed that is equipped with an airflow sensor 56 and/or a nasal thermistor 58. The patient may also be connected to other devices, such as a SaO2 monitor 60, a microphone 62, and/or an actigraph 64, among others. Using various methods of mathematical, analytical, and Fourier transform analyses, 3-dimensional images can be produced in a real-time fashion which can be captured via one or more varieties of computational and computerized methods. In this way, patterns, quantitative degrees, and locations of upper airway narrowing can be assessed in a real-time fashion.

For example, data received from the device 10 may be coupled with data received from one or more of the EEG 52 (for monitoring sleep stage), the plethysmograph 54 (for measuring changes in volume resulting from fluctuations in the amount of air within the airway), electrocardiogram, EOG, and/or the airflow sensor 56 (for monitoring ventilatory cycle). Additionally or alternatively, the actigraph 64 may be used on the patient simultaneously with the collection of the ultrasound images using the device 10 so as to allow assessment of the patient's body position during the sleep study. In this way, embodiments of the device 10 allow for real-time assessment of upper airway collapse during various sleep stages (both non-REM and REM) and in various body positions experienced by the patient during natural sleep using a 4-dimensional analysis. Such data may be coupled with still other airway data (e.g., using an appropriately-titrated MATRx airway device) to determine the degree of airway expansion needed for resolution of OSA for any given age, gender, body mass index, ethnicity, neck circumference, and/or severity of OSA.

Embodiments of the device described herein may thus allow (in a very practical, cost-efficient, and easily-applied fashion) the real-time assessment of airway collapse correlated to stage of sleep, phase of respiration, and body position in any given individual with OSA. For example, although embodiments of the device described herein may be used in a sleep laboratory, hospital, or other medical care institution, embodiments of the device may, in some cases, be configured for use by a patient in the comfort of their own home, thereby allowing the patient to obtain data reflective of the patient's real sleep condition and environment with minimal affect on the patient, such as through the use of wireless communication of the data being collected. Moreover, once a statistically sufficient number of subjects within a specified population has been studied, the resulting population specific data may eliminate the need for expensive and time-consuming titration sleep studies and may in turn serve as a basic method and standard for predicting response to OSA therapy using only imaging data-both for nonsurgical as well as surgical treatment modalities as described in, for example, U.S. Pat. No. 7,697,968, entitled System and Method of Predicting Efficacy of Tongue-based Therapies, the disclosure of which is hereby incorporated herein by reference in its entirety.

Figure 7A:
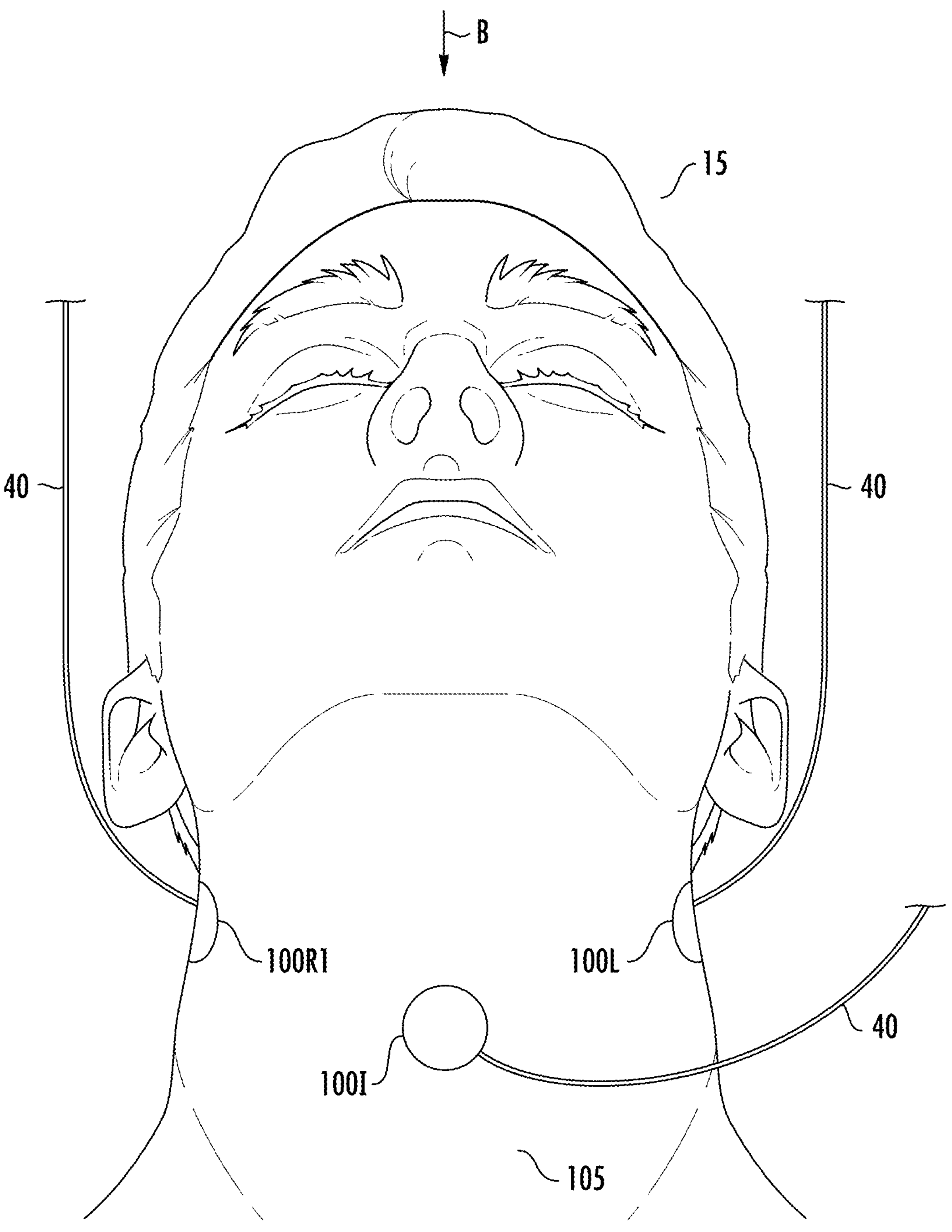
FIG. 7A is a view from above a patient's head and neck with separate ultrasound transducer arrays applied to a plurality of portions of the patient's neck for imaging of the upper airway in some embodiments according to the invention.

FIG. 7A is a perspective view of a patient's 15 head and neck with right ultrasound transducer array 100R1 and left ultrasound transducer array 100L separated from one another on opposing sides of the upper airway 105. The ultrasound transducer arrays 100R1 and 100L are separated from one another so that the transmitted ultrasound beams generated therefrom travel in directions which intersect one another. In other words, in some embodiments according to the invention, the first and second ultrasound transducer arrays 100R1 and 100L are decoupled from one another so that they may be positioned independently to provide acceptable imaging of the upper airway 105. It will be understood that adequate imaging of the upper airway may be provided by imaging from a number of different directions, such as from two opposing sides of the airway. In some embodiments, adequate imaging may be provided with additional (i.e., more than two) transducer arrays positioned on the neck to image from additional directions (i.e., other than directly opposing one another on opposite sides of the airway). In some embodiments, adequate imaging may be provided by positioning transducer arrays on the neck to image the airway from all directions so that the entire perimeter of the airway anatomy is impinged by transmit ultrasound beams. It will be further understood that the inclusion of additional ultrasound transducer arrays may create overlapping portions of the airway to be included in multiple ones of the volumetric ultrasound imaging data sets, the duplication of which may be removed by post processing.

In some embodiments according to the invention, the ultrasound transducer arrays 100R1 and 100L can be located on directly opposing sides of the airway 105. However, as appreciated by the present inventors, the anatomy of the upper airway 105 may vary from patient to patient, so the ultrasound transducer arrays 100R1 and 100L can be positioned independently of one another to accommodate a wide range of anatomies of the upper airway 105 from patient to patient.

It will be understood that the ultrasound transducer arrays 100R1 and 100L can be configured to have more than 1 degree of freedom of movement relative to one another in the 3-D space in which the patient's upper airway 105 is to be imaged. In other words, in some embodiments according to the invention, the ultrasound transducer arrays 100R1 and 100L can be located on different substrates having an adhesive backing such that they may be positioned independently of one another relative to the patient's upper airway 105.

As described above, the ultrasound transducer arrays can be provided in any configuration and size which is convenient for the imaging application desired. For example, in some embodiments according to the invention, the ultrasound transducer arrays 100R1 or 100L can be piezoelectric, CMUT, PMUT, or other types of ultrasound transducer arrays. Moreover, the shape of the ultrasound transducer arrays 100R1 and 100L, can be customized to provide improved imaging for the upper airway 105.

As further shown in FIG. 7A, in some embodiments according to the invention, additional ultrasound transducer arrays may be utilized with the ultrasound transducer arrays 100R1 and 100L. In particular, an intermediate ultrasound transducer array 100I can be included along with the ultrasound transducer arrays 100R1 and 100L. Accordingly, the intermediate ultrasound transducer array 100I can be used to image the upper airway 105 from an additional direction. It will be further understood that any number of ultrasound transducer arrays can be utilized to image the upper airway 105 from a respective number of different directions. As further shown in FIG. 7A, each of the ultrasound transducer arrays 100R1, 100I, and 100L can be coupled to a processor using a respective wire lead 40.

Figure 7B:
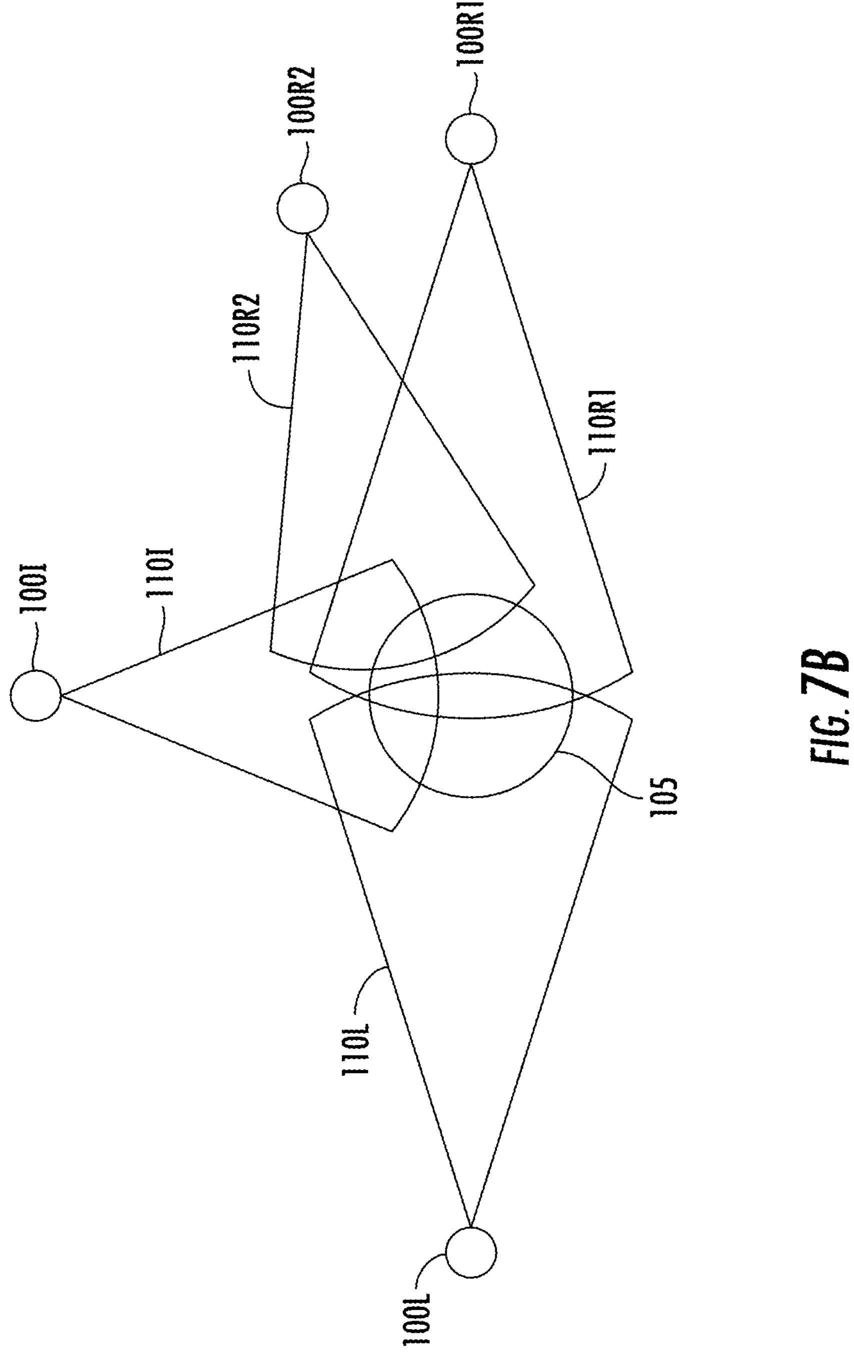
FIG. 7B is a schematic representation of the view labeled B in FIG. 7A showing the positioning of the plurality of separate ultrasound transducer arrays used to generate separate real-time volumetric ultrasound image data sets for imaging of the patient's upper airway in some embodiments according to the invention.

FIG. 7B is a schematic illustration of a plurality of ultrasound transducer arrays positioned separately relative to the upper airway 105 each of which is used to generate a respective volumetric ultrasound data set. In particular, the left ultrasound transducer array 100L can generate a respective volumetric ultrasound image data set 110L, the right ultrasound transducer array 100R1 can generate a respective volumetric ultrasound image data set 110R1, the intermediate ultrasound transducer arrays 100I can generate a respective volumetric ultrasound image data set 1101, and further, a second right ultrasound transducer array 100R2 can generate a respective volumetric ultrasound image data set 110R2. It will be understood that that each of the ultrasound transducer arrays can be operated using "pulse-echo" volumetric imaging to generate the respective volumetric ultrasound image data set.

It will be understood that that the second right ultrasound transducer array 100R2, shown in FIG. 7B, is not visible in FIG. 7A. In other words, FIG. 7B illustrates that additional ultrasound transducer arrays may be used as needed relative to the upper airway 105 to provide adequate volumetric ultrasound image data sets for generating the integrated volumetric image. Accordingly, although only a second right ultrasound transducer array 100R2 is shown, additional ultrasound transducer arrays may be added to the configuration shown in FIG. 7B as needed.

Figure 14:
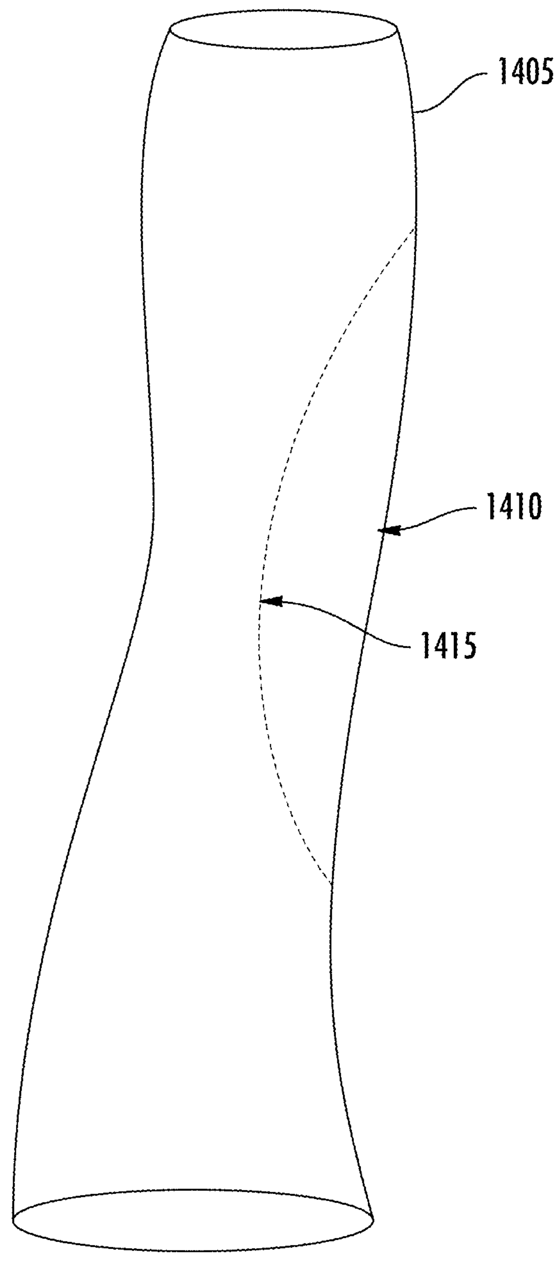
FIG. 14 is a schematic illustration of an integrated volumetric image of a patient's upper airway generated using the first and second ultrasound transducer arrays in some embodiments according to the invention.

As appreciated by the present inventors, because the upper airway 105 contains air, ultrasound transmit beams from the arrays will not translate through the upper airway 105 to the opposite side. Rather, the ultrasound transmit beams generate receive ultrasound beams from the interface in the upper airway 105 that contains air. Accordingly, a plurality of volumetric ultrasound image data sets can be generated and combined with one another to provide an integrated volumetric image that provides a 3-D rendering of the upper airway 105. Furthermore, because the ultrasound imaging system can operate in real time, the integrated volumetric image can be recreated over a time interval to provide a 4-D ultrasound image of the upper airway 105. See, for example, FIG. 14 showing a rendering of an upper airway 105 generated using embodiments according to the present invention.

Figure 8:
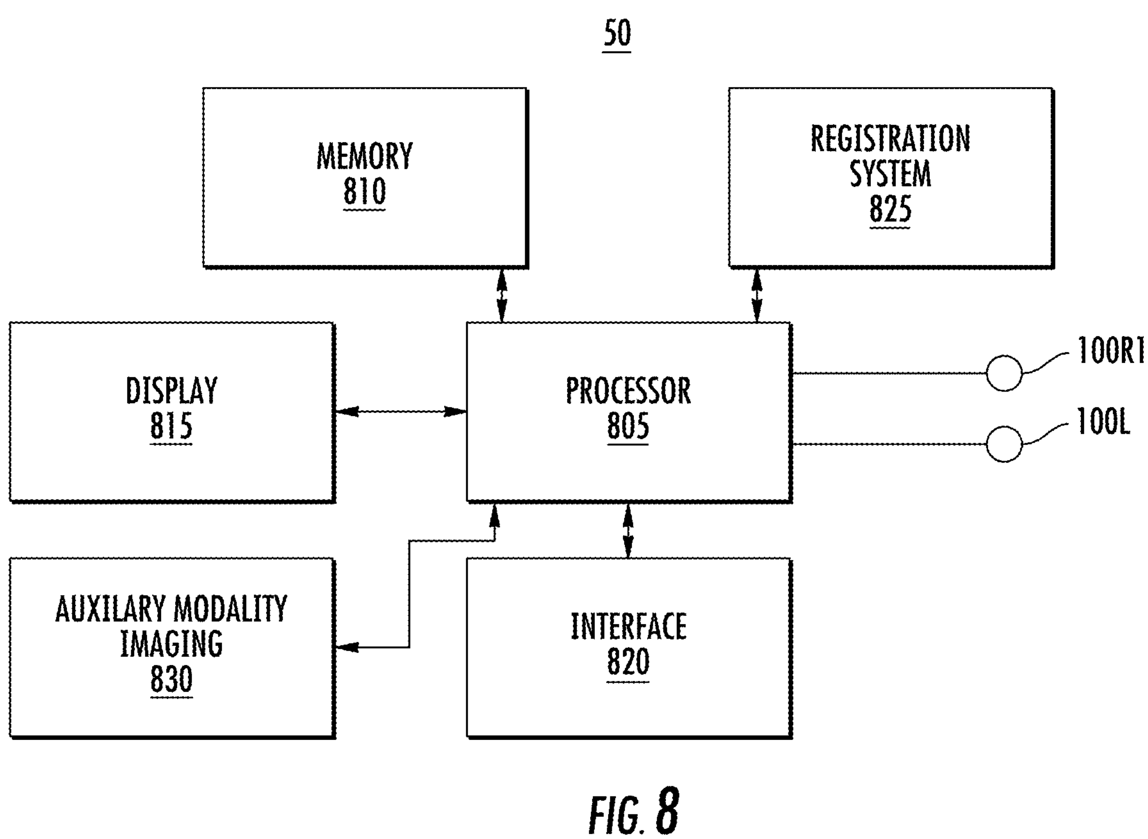
FIG. 8 is a block diagram illustrating a 4D real time ultrasound imaging system in some embodiments according to the invention.

FIG. 8 is a block diagram that illustrates an ultrasound imaging system 50 in some embodiments according to the invention. According to FIG. 8, a processor circuit 805, is coupled to the right ultrasound transducer array 100R1 and to the left ultrasound transducer array 100L. The processor circuit 805 is used to excite the ultrasound transducer arrays 100R1 and 100L to generate transmit ultrasound beams into the upper airway 105. It will be understood that although two ultrasound transducer arrays are shown coupled to the processor circuit 805, any number of ultrasound transducer arrays may be utilized in any desired shape and configuration relative to the upper airway 105. It will be understood that the any of the ultrasound transducer configurations or types described herein can be utilized by the any of the systems described herein.

The receive ultrasound beams are formed by the processor circuit 805 based on the reflections from the transmit ultrasound beams provided to the upper airway 105. In turn, the processor circuit 805 can generate volumetric ultrasound image data sets for each of the ultrasound transducer arrays based on the respective receive ultrasound beams. Furthermore, the processor circuit 805 can store the volumetric ultrasound image data sets in a memory 810 that is coupled thereto. It will be further understood that the memory 810 can also store instructions used to carry out operations of the processor circuit 805 and other subsystems of the ultrasound imaging system 50.

It will be further understood that the processor circuit 805 is configured to combine the volumetric ultrasound image data sets generated using the ultrasound transducer arrays to provide an integrated volumetric image. For example, in some embodiments according to the invention, the different volumetric ultrasound image data sets are overlaid with one another in a coordinate space, so as to generate the integrated volumetric image as shown in FIG. 14.

The processor circuit 805 is also coupled to a display 815 that may be utilized by the operator to generate the volumetric ultrasound image data sets and otherwise interact with operations of the ultrasound imaging system 50 such as adjusting the positions of the ultrasound transducer arrays that are to be utilized for a particular patient.

FIG. 8 also illustrates that the ultrasound imaging system 50 includes a registration system 825 that provides positions of the ultrasound transducer arrays relative to one another in the 3-dimensional (3D) space in which the ultrasound transducer arrays are deployed. Accordingly, the processor circuit 805 uses the registration system 825 to determine the relative locations of the ultrasound transducer arrays to accurately combine the respective volumetric ultrasound image data sets with one another to provide the integrated volumetric image. It will be understood that that the combination of the volumetric ultrasound image data sets can be provided as described in, for example, *Combining multiple true 3D ultrasound image volumes through re-registration and rasterization*, Ji S1, Roberts D W, Hartov A, Paulsen K D, Med Image Comput Comput Assist Interv. 2009; 12 (Pt 1): 795-802, the disclosure of which is incorporated herein by reference.

Figure 9:
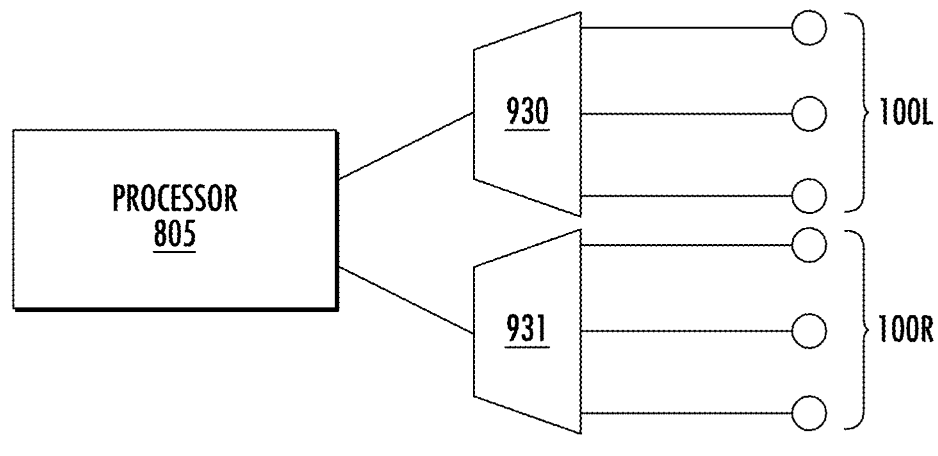
FIG. 9 is a block diagram illustrating a switching circuit configured to couple the plurality of ultrasound transducer arrays positioned on different portions of the patient's neck to the processor circuit, for example, as part of a registration process for the ultrasound transducer arrays in some embodiments according to the invention.

FIG. 9 is a block diagram which illustrates switching circuits 930 and 931 used to couple the processor circuit 805 to a plurality of ultrasound transducer arrays 100L and 100R. In particular, the switching circuit 930 is used to switch among a plurality of ultrasound transducer arrays 100L that may be located, for example, on the left side of the upper airway 105 whereas the switching circuit 931 may be used to switch among a plurality of ultrasound transducer arrays 100R that are located on the right side of the upper airway 105. In operation, the processor circuit 805 can select which of the ultrasound transducer arrays in the plurality located on the left side of the upper airway 105 is to be utilized for imaging. Similarly, the processor circuit 805 can use the switching circuit 931 to switch between the plurality of ultrasound transducer arrays 100R that are located on the right side of the upper airway 105. It will be understood that, in some embodiments according to the invention, the functionality of the switching circuits 930 and 931 can be provided software enablement of redundant circuits.

Therefore, when operating the ultrasound transducer arrays, the processor circuit 805 can switch between the plurality of ultrasound transducer arrays located on each side of the upper airway 105. Such operations may be used, for example, to determine which of the ultrasound transducer arrays may be utilized to provide the best volumetric ultrasound image data sets for generation of the integrated volumetric image. Still further, the processor circuit 805 may operate all of the ultrasound transducer arrays within each of the respective pluralities to image the upper airway so that the switching circuits 930 and 931 are used to cycle through each of the ultrasound transducer arrays for generation of the volumetric ultrasound image data sets and therefore the integrated volumetric image. It will be understood that the ultrasound transducer arrays within each of the respective pluralities can operate at the same time or may be staggered to reduce interference. Different frequencies may also be used for the ultrasound transducer arrays within each of the respective pluralities.

Figure 10:
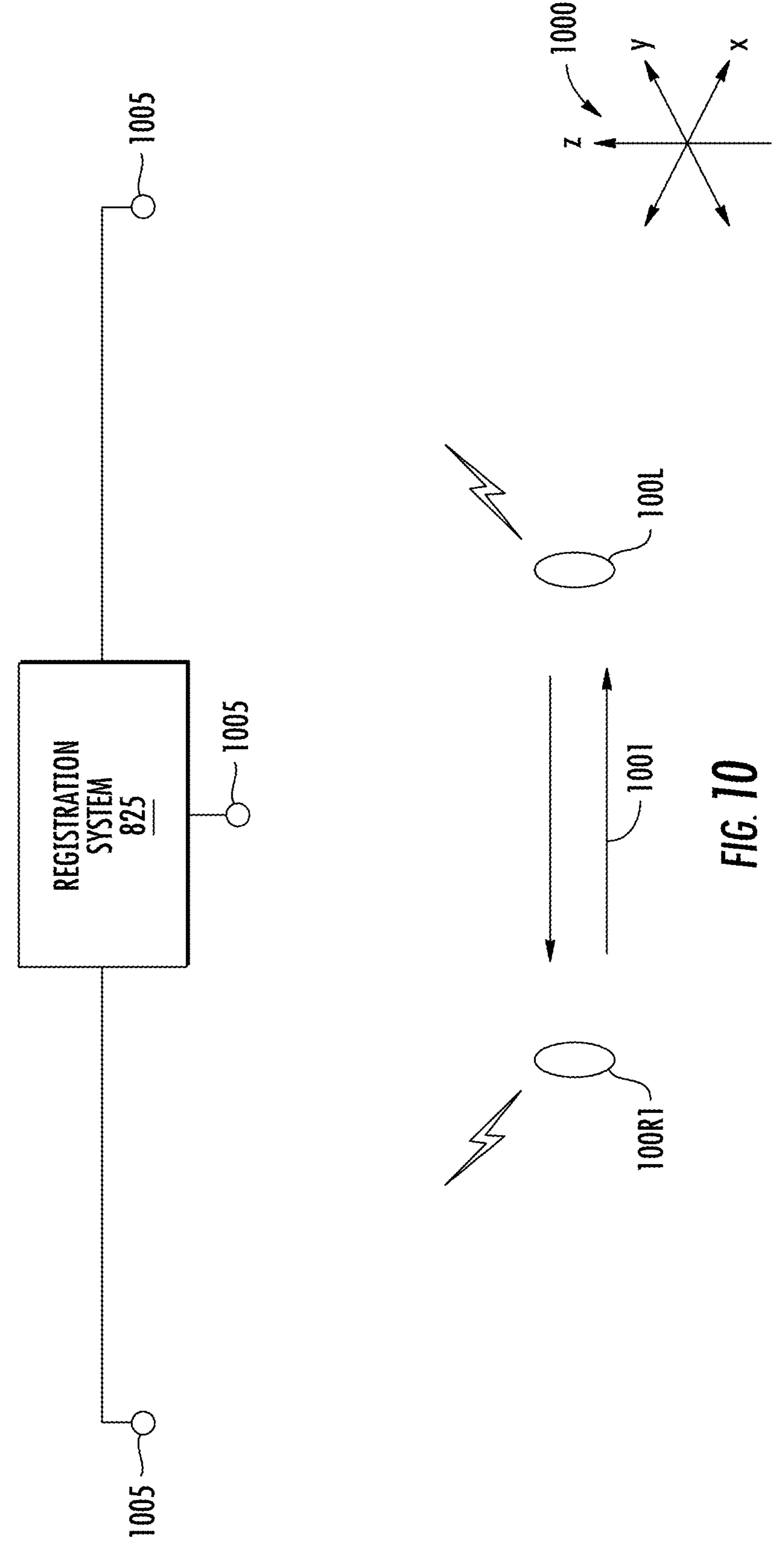
FIG. 10 is a schematic illustration of the registration system shown in FIG. 8 configured to utilize optical, ultrasound, radio, and/or magnetic based registration in some embodiments according to the invention.

FIG. 10 is a schematic illustration of the registration system 825 shown in FIG. 8 in some embodiments according to the invention. According to FIG. 10, the registration system 825 is utilized to determine the relative positions of each of the ultrasound transducer arrays utilized by the ultrasound imaging system for imaging of the upper airway 105. For example, when the right and left ultrasound transducer arrays 100R1 and 100L are placed separated from one another opposite the upper airway 105, the registration system 825 is used to determine the respective locations of each of the ultrasound transducers relative to one another. It will be understood that the registration system 825 can use any suitable technique to determine the location of each of the ultrasound transducer arrays deployed. For example, the registration system 825 may use optical, radio, magnetic, or other types of sensing systems to determine the positions of the ultrasound transducer arrays relative to one another.

Still further, the registration system 825 may utilize ultrasound data transmitted from one of the ultrasound transducer arrays to the other. In such an approach, one of the ultrasound transducer arrays may transmit a particular phased sequence of ultrasound data into the tissue around the upper airway 105. The ultrasound transducer array located opposite the transmitting ultrasound transducer array, can detect the transmitted ultrasound data and determine the direction from which an orientation of the transmitting ultrasound array. This ultrasound data may be utilized to determine the relative positions of the ultrasound transducer arrays to one another in the space in which the upper airway 105 is to be imaged. In some embodiments according to the invention, other techniques can be used by the registration system 825, such as an acoustic approach.

It will be further understood that in some embodiments according to the invention, the registration system 825 can determine the position of each of the ultrasound transducer arrays within six degrees of freedom of movement 1000 in the 3-dimensional space in which the ultrasound transducer arrays are positioned relative to one another. It will be understood that that the registration of the ultrasound transducer arrays can be provided as described in, for example, Intra-Operative Position Sensing and Tracking Devices, D. A. Simon, Ph.D, Center for Orthopaedic Research, Shadyside Hospital, Pittsburgh, PA, USA and Center for Medical Robotics and Computer Assisted Surgery, Robotics Institute, Carnegie Mellon University, Pittsburgh, PA, USA, the disclosure of which is incorporated herein by reference. It will be understood that registration systems according to the present invention can utilize any type of technique to determine relative positions of the arrays (using, for example angles between the arrays), such as acoustic, inertial, LED, magnetic or reflective indicia, or combinations of any of these, to determine the relative locations, for example, at two times the frequency rate of the desired motion, or more. Related systems are described in, for example, U.S. Pat. No. 9,138,319, entitled Method and system for aligning a prosthesis during surgery, the disclosure of which is incorporated herein by reference.

Figure 11:
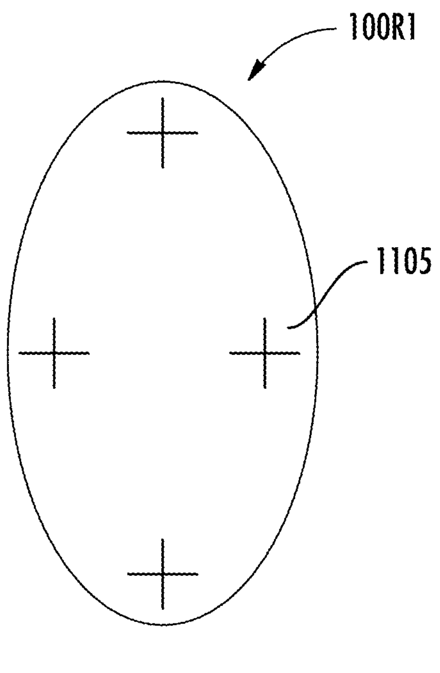
FIG. 11 is a schematic illustration of an ultrasound transducer array having indicia included thereon used to determine position of the ultrasound transducer array in a 3-dimensional space in which the ultrasound transducer array is deployed in some embodiments according to the invention.

FIG. 11 is a schematic illustration of a representative ultrasound transducer array 100R1 having indicia 1105 located thereon in some embodiments according to the invention. According to FIG. 11, the ultrasound transducer array 100R1 may have indicia 1105 located thereon to assist the registration system 825 in determining the position of the ultrasound transducer array 100R 1 within the 3D space in which the upper airway 105 is to be imaged. Accordingly, the registration system may use an optical system to recognize the indicia 1105 and determine the position (with six degrees of freedom 1000) of the ultrasound transducer array 100R1 based thereon. It will be understood that that the recognition of indicia can be provided as described in, for example, U.S. Pat. No. 9,405,971, entitled Object-Tracking systems and methods, the disclosure of which is incorporated herein by reference.

Figure 12:
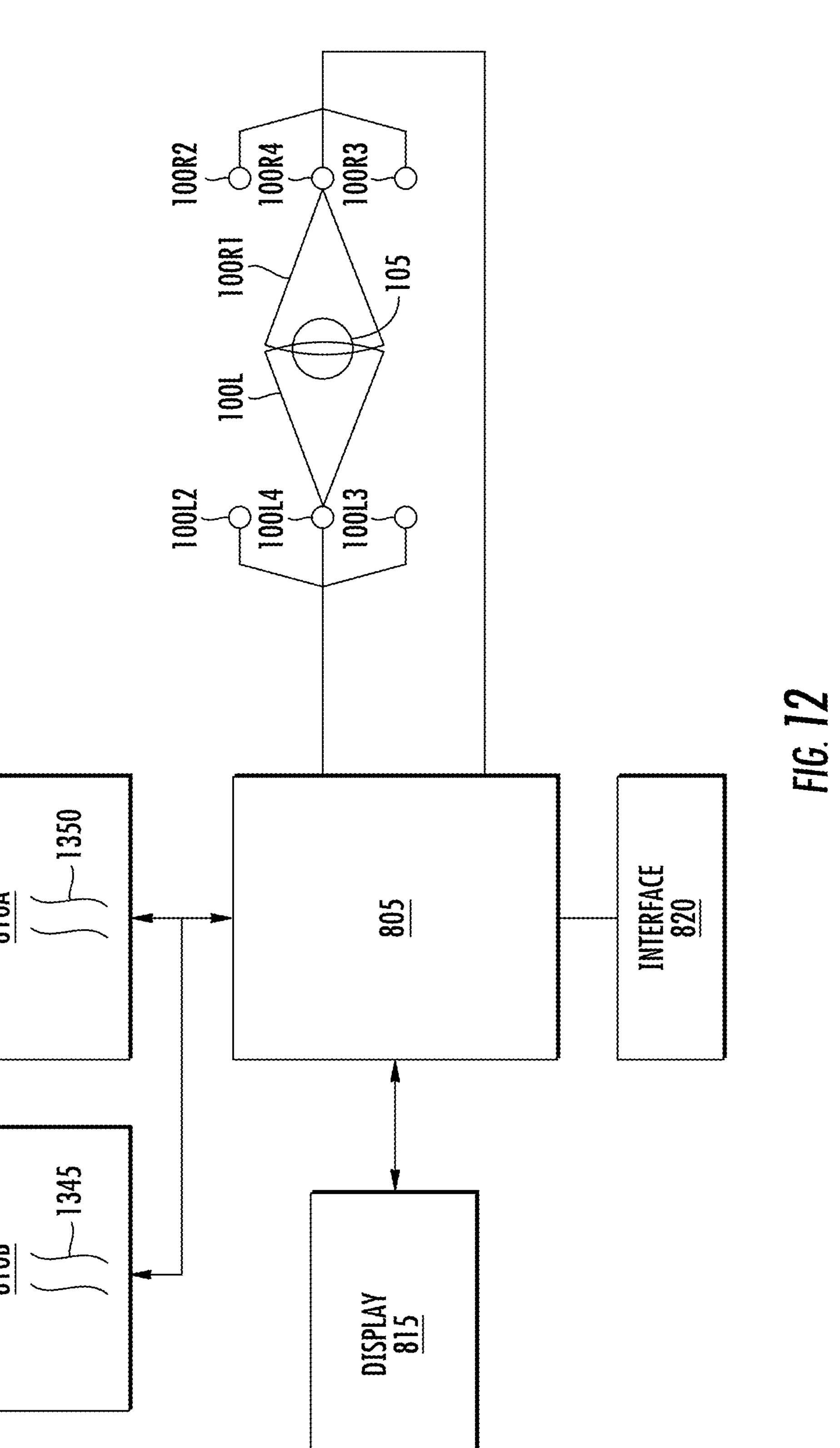
FIG. 12 is a block diagram illustrating an ultrasound imaging system using a registration system including a plurality of candidate transducer arrays used to generate a registration image that can be compared to a pre-determined anatomical construct for automatic or semi-automatic registration of the ultrasound imaging system in some embodiments according to the invention.

FIG. 12 is a block diagram of an ultrasound imaging system utilizing a registration system based on a comparison to a pre-determined anatomical construct in some embodiments according to the invention. According to FIG. 12, the processor circuit 805 is coupled to an array of left ultrasound transducers 100L and a plurality of right ultrasound transducers 100R. It will be understood, however, that additional ultrasound transducers may also be used. In some embodiments according to the invention, other approaches may be used, such as optical or acoustical approaches. Other approaches may also be used.

The processor circuit 805 can switch among each of the plurality of ultrasound transducers located on the left and right sides of the upper airway 105 (see for example, FIG. 9). The selection can be used to determine which of the ultrasound transducer arrays on both sides provides the best imaging for the upper airway 105. For example, the processor circuit 805 may select the ultrasound transducer array 100L1 as a candidate on the left side, and the ultrasound transducer array 100R1 as a candidate on the right side of the upper airway 105. The processor circuit 805 may then carry out imaging of the upper airway 105 using the two candidate ultrasound transducer arrays and generate perspective volumetric ultrasound image data sets to provide a registration volumetric image 1330 which may be stored in the memory 810*a*.

The registration image 1330 can then be compared to a pre-determined anatomical construct 1345 of an upper airway. In other words, the pre-determined anatomical construct 1345 may correspond to a typical or idealized upper airway and the integrated volumetric image 1330 generated by the candidate ultrasound transducer arrays can be compared to the pre-determined anatomical construct 1345 to determine the level of match therebetween. The processor circuit 805 can then store the results of the match and then cycle to the next pair of candidates of ultrasound transducer arrays used to generate respective volumetric ultrasound image data sets. Subsequently, the processor circuit 805 can then generate a comparison to the pre-determined anatomical construct 1345 which may then be stored in the memory 810*a*. The processor circuit 805 may then cycle through all of the ultrasound transducer arrays as candidates and determine which of the ultrasound transducer arrays provides the best match to the pre-determined anatomical construct 1345. Accordingly, the ultrasound imaging system 50 may use a self-registration system by selecting the best ultrasound transducer arrays among all of the candidates.

In some embodiments, a technician or operator may utilize the ultrasound imaging system 50 to aid in the selection of the best match between the pre-determined anatomical construct 1345 and each of the registration images 1330.

Still referring to FIG. 8, the system 50 can also include, or be coupled to, an auxiliary imaging modality 830, such as cone beam CT scanner or medical grade CT scanner. The combination of the auxiliary imaging modality 830 with the 4D real time ultrasound imaging system 50 may help improve the treatment of patients certain conditions, such as obstructive sleep apnea (OSA). As appreciated by the present inventors, the upper airway may be prone to collapse during supine REM sleep in subjects with OSA. In some embodiments, the 4D real time ultrasound system can provide 4D images of the upper airway on subjects during both upright wakefulness and supine natural sleep (both during REM and non-REM sleep). In particular, supine REM sleep may be the body position and stage of sleep in which upper airway obstruction may be most commonly observed. 4D real time ultrasound images of the upper airway obtained during upright wakefulness, compared with images of the upper airway during supine natural sleep may allow comparison and determination of the change in the minimal airway size and airway shape between these two states. Similarly, the change in minimal airway size with the mandible at rest and at its fully protruded state (during both upright wakefulness and supine sleep) can be obtained.

A CT scan of the upper airway and facial skeleton (obtained during upright wakefulness) using a cone beam CT scanner may provide a fixed (or average) image of the upper airway obtained during a 12-14-second revolution/scan of the patient during upright wakefulness (this 12-14 second scan, performed while the patient is ventilating, may produce an “average” of soft tissue movement resulting from the normal wakefulness ventilatory cycle). Skeletal, as well as soft tissue imaging data may be obtained during this wakefulness scan, and the skeletal (hard tissue) data often used in planning purposes for skeletal surgical planning in surgical airway expansion.

Furthermore, upper airway data can be obtained using the 3D cone beam scanner during upright wakefulness as well as during upright wakefulness. The change in the average minimal airway size induced through mandibular protrusion (compared with the mandible at rest) during upright wakefulness can be measured as the difference between these two scans but may not be correlated to minimal airway size during supine REM sleep, or to how much expansion in minimal airway size is required during supine REM sleep is required to eliminate OSA.

As appreciated by the present inventors, the difference in minimal airway size between upright wakefulness (both with the mandible at rest, as well as with the mandible protruded) compared with the minimal airway size during supine REM sleep- and the amount of expansion of the minimal airway size that is required during supine REM sleep to eliminate OSA may be problematic. As appreciated by the present inventors, it would be of benefit to the treating clinician to know how much expansion in minimal airway size is needed in the upright wakefulness airway (for any given age/gender/BMI/neck circumference/and ethnicity) to achieve adequate upper airway minimal airway size expansion during supine REM sleep sufficient to, for example, eliminate OSA.

Accordingly, the 4D real time ultrasound system 50 may allow the clinician to calculate the change in minimal airway size from upright wakefulness to supine REM sleep. And, thorough use of titration devices, the amount of incremental minimal airway size expansion during supine REM sleep needed to eliminate OSA may be calculated.

Therefore, the 4D ultrasound upper airway data might be integrated with the static 3D cone-beam CT scan upper airway data (or other modality imaging), such that by manipulating the cone beam skeletal data, the resulting change in soft tissue airway minimal airway size can be seen in an incremental and accurate fashion without the need for multiple ionizing radiation images of the patient.

Integration of the upright 4D ultrasound upper airway imaging data with the upright 3D cone beam CT data using a “best fit” overlay of the two images can be provided by comparing the two images (the 3D cone beam CT upper airway wakefulness image vs. the 4D ultrasound upper airway wakefulness image, obtained with the mandible at rest), identifying common landmarks, and accurately replacing the upright mandibular rest position 3D CBCT data with the 4D ultrasound upright mandibular rest position wakefulness data so that the data can be accurately aligned in all three planes of space. A similar set of image replacements with the mandible in the fully advanced position during wakefulness may also be performed so that the cone beam CT data is subsequently replaced with the 4D ultrasound data. The 4D ultrasound upper airway imaging data may then compared with the supine REM sleep airway data, and comparisons of minimal airway size may be obtained.

Figure 13:
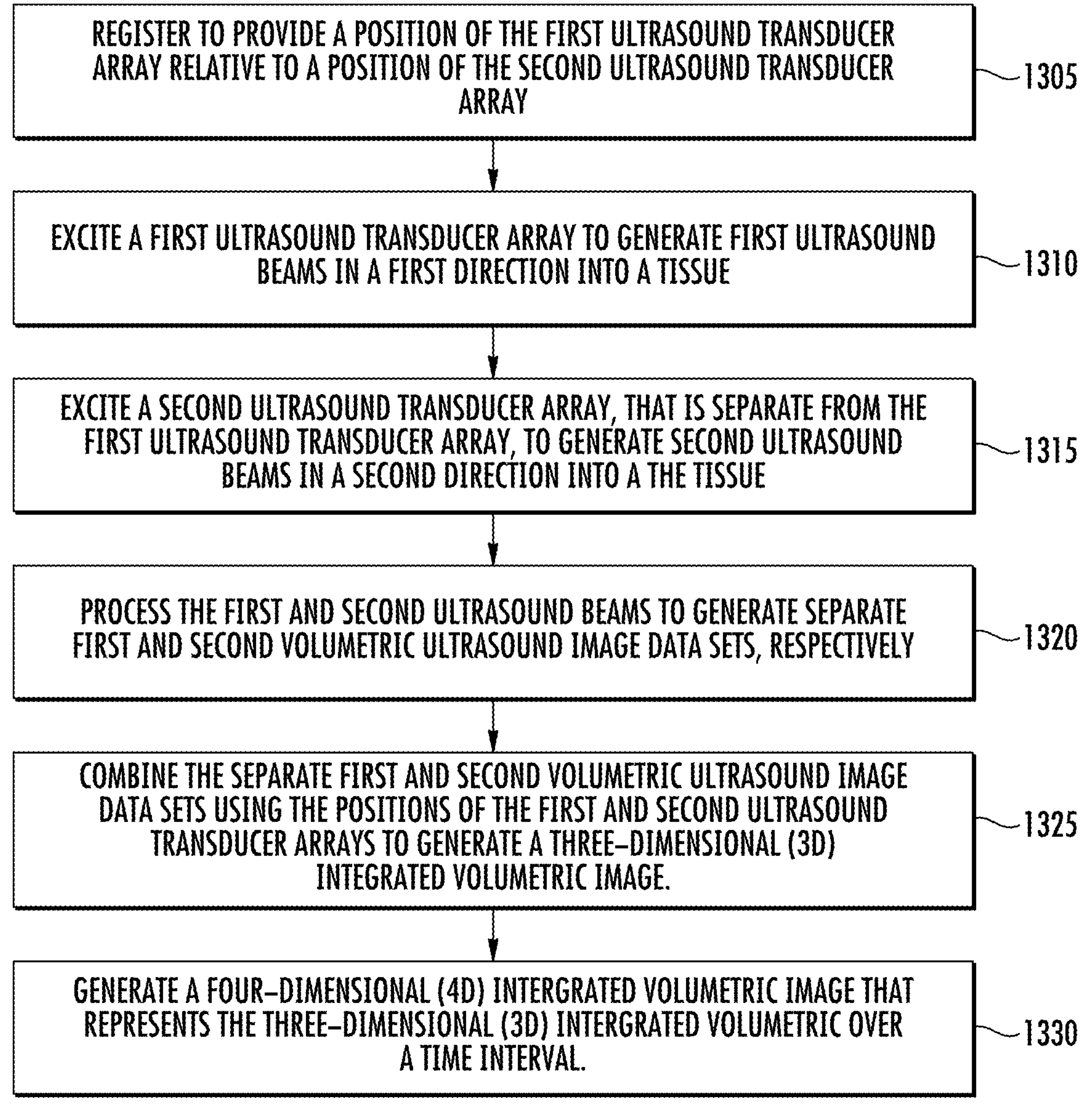
FIG. 13 is a flow chart illustrating operations of an ultrasound imaging system in some embodiments according to the invention.

FIG. 13 is a flowchart which illustrates operations of an ultrasound imaging system 50 in some embodiments according to the invention. According to FIG. 13, the ultrasound imaging system 50 registers the positions of the ultrasound transducer arrays to be used for imaging of the upper airway 105 to provide the positions of each of the ultrasound transducer arrays relative to one another (Block 1305).

The processor circuit 805 then excites the first ultrasound transducer array to generate first steered ultrasound beams in a first direction into the tissue (Block 1310). The processor circuit 805 also excites the second ultrasound transducer array, which is separate from the first ultrasound transducer array, to generate second steered ultrasound beams in a second direction into the tissue (Block 1315).

The processor circuit 805 then processes the first and second ultrasound beams generated by the steered ultrasound beams to generate separate first and second volumetric ultrasound image data sets respectively (Block 1320). The processor circuit 805 can then combine the separate first and second volumetric ultrasound image data sets using the positions of the first and second ultrasound transducer arrays (generated by the registration system 825) to generate a 3-dimensional integrated volumetric image therefrom (Block 1325). Then, the processor circuit 805 can generate a 4-dimensional integrated volumetric image that represents the 3-dimensional integrated volumetric image over a time interval as shown for example in FIG. 14 (Block 1330).

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present inventive subject matter. As used herein, the term “and/or” includes any and all combinations of one or more of the associated listed items.

It will be understood that when an element is referred to as being “connected” or “coupled” to another element, it can be directly connected or coupled to the other element or intervening elements may be present. In contrast, when an element is referred to as being “directly connected” or “directly coupled” to another element, there are no intervening elements present.

It will be understood that when an element or layer is referred to as being “on” another element or layer, the element or layer can be directly on another element or layer or intervening elements or layers may also be present. In contrast, when an element is referred to as being “directly on” another element or layer, there are no intervening elements or layers present. As used herein, the term “and/or” includes any and all combinations of one or more of the associated listed items.

Spatially relative terms, such as “below”, “beneath”, “lower”, “above”, “upper”, and the like, may be used herein for ease of description to describe one element or feature’s relationship to another element(s) or feature(s) as illustrated in the figures. It will be understood that the spatially relative terms are intended to encompass different orientations of the device in use or operation, in addition to the orientation depicted in the figures. Throughout the specification, like reference numerals in the drawings denote like elements.

Embodiments of the inventive subject matter are described herein with reference to plan and perspective illustrations that are schematic illustrations of idealized embodiments of the inventive subject matter. As such, variations from the shapes of the illustrations as a result, for example, of manufacturing techniques and/or tolerances, are to be expected. Thus, the inventive subject matter should not be construed as limited to the particular shapes of objects illustrated herein, but should include deviations in shapes that result, for example, from manufacturing. Thus, the objects illustrated in the figures are schematic in nature and their shapes are not intended to illustrate the actual shape of a region of a device and are not intended to limit the scope of the inventive subject matter.

The terminology used herein is for the purpose of describing particular embodiments only and is not intended to be limiting of the present inventive subject matter. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this present inventive subject matter belongs. It will be further understood that terms used herein should be interpreted as having a meaning that is consistent with their meaning in the context of this specification and the relevant art and will not be interpreted in an idealized or overly formal sense unless expressly so defined herein. The term "plurality" is used herein to refer to two or more of the referenced item.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computer environment or offered as a service such as a Software as a Service (SaaS).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/BlueRay).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and/or flowchart block or blocks. Accordingly, embodiments of the present inventive concepts may be embodied in hardware and/or in software (including firmware, resident software, micro-code, etc.) that runs on a processor such as a digital signal processor, which may collectively be referred to as "circuitry," "a module," or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

Many different embodiments have been disclosed herein, in connection with the above description and the drawings. It will be understood that it would be unduly repetitious and obfuscating to literally describe and illustrate every combination and subcombination of these embodiments. Accordingly, the present specification, including the drawings, shall be construed to constitute a complete written description of various example combinations and subcombinations of embodiments and of the manner and process of making and using them, and shall support claims to any such combination or subcombination.

Many modifications and other embodiments of the inventions set forth herein will come to mind to one skilled in the art to which these inventions pertain having the benefit of the teachings presented in the foregoing descriptions and the associated drawings. For example, although the embodiments illustrated in the figures show two rectangular electrode strips placed on either side of the patient's neck, a single, longer electrode strip (e.g., twice as long) may be provided that extends from one side of the patient's neck to the other (e.g., across the patient's throat). As yet another example, two or more circular electrode strips may be arranged around the patient's neck, such as electrode strips that are approximately between 5 and 10 mm in diameter. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A system for imaging tissue, the system comprising:

first and second ultrasound transducer arrays configured to secure to first and second surface locations, respectively, the first and second ultrasound transducer arrays being positioned in relation to tissue at different surface locations such that ultrasound beams from the first and second ultrasound transducer arrays propagate into the tissue from different directions; and a processor circuit operatively coupled to the first and second ultrasound transducer arrays, the processor circuit configured to operate the first and second ultrasound transducer arrays for pulse-echo imaging of the tissue, to generate respective first and second volumetric ultrasound image data sets in real-time corresponding to different respective portions of the tissue that are limited by acoustic shadowing relative to the respective ultrasound transducer arrays, and to provide an integrated volumetric image of the tissue from the first and second surface locations by combining the first and second volumetric ultrasound image data sets to include portions of the tissue not observable from a single one of the ultrasound transducer arrays.

2. The system of claim 1, wherein the first and second surface locations correspond to a first side and a second side of a neck, respectively, and the tissue comprises a soft tissue-airway interface for assessing obstructive sleep apnea (OSA).

3. The system of claim 1, wherein the first volumetric ultrasound image data set includes pulse-echo image data that corresponds to a first portion of the tissue that is closest to the first ultrasound transducer array and is free of image data that corresponds to tissue that is in a shadow of the first portion relative to the first ultrasound transducer array; and wherein the second volumetric ultrasound image data set includes pulse-echo image data that corresponds to a second portion of the tissue that is closest to the second ultrasound transducer array and is free of image data that corresponds to the tissue that is in a shadow of the second portion relative to the second ultrasound transducer array.

4. The system of claim 1, further comprising:

additional ultrasound transducer arrays, spaced apart from the first and second ultrasound transducer arrays, the additional ultrasound transducer arrays configured to secure to other surface locations, wherein each of the additional ultrasound transducer arrays is configured to transmit and receive ultrasound beams for pulse-echo imaging of the tissue from the other surface locations.

5. The system of claim 1, wherein the first ultrasound transducer arrays and the second ultrasound transducer arrays are part of the same ultrasound imaging system.

6. The system of claim 1, wherein the first ultrasound transducer array comprises an array of ultrasound transducers supported by a body member configured to be secured to a surface location via an adhesive layer.

7. The system of claim 1, further comprising a registration system, wherein the registration system determines relative positions of the first and second ultrasound transducer arrays in three-dimensional space.

8. The system of claim 1, wherein the processor circuit is operatively coupled to at least one of an EEG, plethysmograph, electrocardiogram, electromyogram (EMG), electrooculogram (EOG), nasal thermistor airflow sensor, nasal pressure airflow sensor, inductance plethysmography belt, oxygen saturation (SaO2), surrogate marker of REM sleep, pulsatile arterial tomography (PAT signal), microphone for detection of snoring, real-time apnea detection device, or an actigraph.

9. The system of claim 1, further comprising a third ultrasound transducer array configured to secure to a third surface location, the third ultrasound transducer array being positioned in relation to the tissue, wherein the processor circuit is configured to operate the third ultrasound transducer array for pulse-echo imaging of the tissue, to generate a third volumetric ultrasound image data set, the processor circuit generates the integrated volumetric image of the tissue based on the first, second, and third volumetric ultrasound image data sets.

10. The system of claim 1, wherein the first and second volumetric ultrasound image data sets are each generated in real-time with reference to a time interval, and wherein generating the integrated volumetric image comprises integrating the first and second volumetric ultrasound image data sets with reference to the time interval.

11. The system of claim 1, wherein the first and second ultrasound transducer arrays are positionable on the tissue independently of a common supporting structure that fixes a relative position between the arrays.

* * * * *